United States Patent
Trissel et al.

(10) Patent No.: US 7,678,127 B2
(45) Date of Patent: *Mar. 16, 2010

(54) MULTI-LANCET DEVICE WITH STERILITY CAP REPOSITIONING MECHANISM

(75) Inventors: John Trissel, Canton, GA (US); Richard W. LeVaughn, Newnan, GA (US); Gwenn E. Kennedy, Ellenwood, GA (US); Stephen J. Flynn, Peachtree City, GA (US); Carl E. Griffin, Marietta, GA (US); John C. Irwin, Woodstock, GA (US); Mary Kate Pynes, Dallas, GA (US); Stephanie J. Campbell, Kennesaw, GA (US); Christopher J. Ruf, Marietta, GA (US); Mitchell A. Solis, Cumming, GA (US); Avi M. Robbins, Longwood, FL (US); Jason R. Heath, Marietta, GA (US); Ray Lathrop, Atlanta, GA (US); David R. Buenger, Roswell, GA (US); Venkat Katragadda, Marietta, GA (US); Jack Griffis, Decatur, GA (US); Don Griffin, Kennesaw, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 1472 days.

This patent is subject to a terminal disclaimer.

(21) Appl. No.: 10/921,487

(22) Filed: Aug. 19, 2004
(Under 37 CFR 1.47)

(65) Prior Publication Data

US 2005/0149089 A1 Jul. 7, 2005

Related U.S. Application Data

(60) Provisional application No. 60/598,147, filed on Aug. 2, 2004, provisional application No. 60/497,024, filed on Aug. 20, 2003.

(51) Int. Cl.
*A61B 5/151* (2006.01)

(52) U.S. Cl. .................. 606/183; 606/181; 606/182
(58) Field of Classification Search ......... 606/181–183, 606/167–186; 600/583, 584, 192, 295, 263; 604/197, 198, 192, 195, 263; 112/12–153, 112/470.01–470.36, 40; 81/9.22
See application file for complete search history.

(56) References Cited

U.S. PATENT DOCUMENTS 4,627,445 A 12/1986 Garcia et al.

(Continued)

FOREIGN PATENT DOCUMENTS

DE 198 19 407 A1 11/1999

(Continued)

OTHER PUBLICATIONS

Office Action Summary-Non-Final Office Action dated Oct. 1, 2007; 12 pgs.

(Continued)

*Primary Examiner*—Anhtuan T Nguyen
*Assistant Examiner*—Amy T Lang
(74) *Attorney, Agent, or Firm*—Gardner Groff Greenwald & Villanueva, PC

(57) ABSTRACT

A lancing device has a carousel of lancets removably received in a housing. In exemplary embodiments, the lancing device includes a sterility cap positioning mechanism that removes sterility caps from the lancets for actuation and afterwards replaces the sterility caps onto the lancets. Preferably, the lancing device includes a lancet advancing mechanism that automatically advances sequential lancets of the lancet carousel for charging and actuating, and a drive mechanism for actuating the lancets. Also provided are replacement lancet carousels, which include a cylindrical carrier with axial openings and a plurality of the lancets axially oriented in the openings.

21 Claims, 31 Drawing Sheets

U.S. PATENT DOCUMENTS

| | | | |
|---|---|---|---|
| 4,787,398 A | 11/1988 | Garcia et al. | |
| 4,794,926 A | 1/1989 | Munsch et al. | |
| 4,823,806 A | 4/1989 | Bajada | |
| 4,974,926 A | 12/1990 | Blee et al. | |
| 5,279,294 A | 1/1994 | Anderson et al. | |
| 5,318,584 A | 6/1994 | Lange et al. | |
| 5,514,152 A | 5/1996 | Smith | |
| 5,628,765 A | 5/1997 | Morita | |
| 5,741,288 A | 4/1998 | Rife | |
| 5,871,494 A | 2/1999 | Simons et al. | |
| 5,916,230 A * | 6/1999 | Brenneman et al. | 606/172 |
| 5,951,492 A | 9/1999 | Douglas et al. | |
| 5,971,941 A | 10/1999 | Simons et al. | |
| 6,036,924 A | 3/2000 | Simons et al. | |
| 6,071,294 A | 6/2000 | Simons et al. | |
| 6,099,484 A | 8/2000 | Douglas et al. | |
| 6,228,100 B1 * | 5/2001 | Schraga | 606/183 |
| 6,472,220 B1 | 10/2002 | Simons et al. | |
| 6,530,892 B1 | 3/2003 | Kelly | |
| 6,783,537 B1 * | 8/2004 | Kuhr et al. | 606/182 |
| 7,150,755 B2 * | 12/2006 | Levaughn et al. | 606/181 |
| 2002/0087056 A1 | 7/2002 | Aceti et al. | |
| 2003/0073931 A1 | 4/2003 | Boecker et al. | |
| 2003/0083685 A1 | 5/2003 | Freeman et al. | |
| 2003/0199789 A1 | 10/2003 | Boecker et al. | |
| 2003/0199790 A1 | 10/2003 | Boecker et al. | |
| 2003/0199791 A1 | 10/2003 | Boecker et al. | |
| 2003/0199893 A1 | 10/2003 | Boecker et al. | |
| 2003/0199894 A1 | 10/2003 | Boecker et al. | |
| 2003/0199895 A1 | 10/2003 | Boecker et al. | |
| 2003/0199896 A1 | 10/2003 | Boecker et al. | |
| 2003/0199897 A1 | 10/2003 | Boecker et al. | |
| 2003/0199898 A1 | 10/2003 | Boecker et al. | |
| 2003/0199899 A1 | 10/2003 | Boecker et al. | |
| 2003/0199900 A1 | 10/2003 | Boecker et al. | |
| 2003/0199901 A1 | 10/2003 | Boecker et al. | |
| 2003/0199902 A1 | 10/2003 | Boecker et al. | |
| 2003/0199903 A1 | 10/2003 | Boecker et al. | |
| 2003/0199904 A1 | 10/2003 | Boecker et al. | |
| 2003/0199905 A1 | 10/2003 | Boecker et al. | |
| 2003/0199906 A1 | 10/2003 | Boecker et al. | |
| 2003/0199907 A1 | 10/2003 | Boecker et al. | |
| 2003/0199908 A1 | 10/2003 | Boecker et al. | |
| 2003/0199909 A1 | 10/2003 | Boecker et al. | |
| 2003/0199910 A1 | 10/2003 | Boecker et al. | |
| 2003/0199911 A1 | 10/2003 | Boecker et al. | |
| 2003/0212424 A1 | 11/2003 | Briggs et al. | |
| 2004/0009100 A1 | 1/2004 | Simons et al. | |
| 2004/0010279 A1 | 1/2004 | Freeman et al. | |
| 2004/0039303 A1 * | 2/2004 | Wurster et al. | 600/584 |
| 2004/0049220 A1 | 3/2004 | Boecker et al. | |
| 2004/0087990 A1 | 5/2004 | Boecker et al. | |
| 2004/0092944 A1 | 5/2004 | Penenberg | |
| 2004/0092995 A1 | 5/2004 | Boecker et al. | |
| 2004/0098009 A1 * | 5/2004 | Boecker et al. | 606/181 |
| 2004/0102803 A1 | 5/2004 | Boecker et al. | |
| 2005/0015020 A1 * | 1/2005 | LeVaughn et al. | 600/583 |
| 2005/0154410 A1 * | 7/2005 | Conway et al. | 606/181 |
| 2006/0195128 A1 * | 8/2006 | Alden et al. | 606/181 |
| 2006/0235454 A1 * | 10/2006 | LeVaughn et al. | 606/181 |
| 2007/0088377 A1 * | 4/2007 | LeVaughn et al. | 606/181 |
| 2008/0119883 A1 * | 5/2008 | Conway et al. | 606/181 |

FOREIGN PATENT DOCUMENTS

| | | |
|---|---|---|
| DE | 100 57 832 C1 | 2/2002 |
| DE | 10208575 | 2/2002 |
| EP | 0 449 525 A1 | 3/1991 |
| EP | 0 877 250 A2 | 11/1998 |
| EP | 0 949 506 A2 | 10/1999 |
| EP | 0 589 186 B1 | 11/1999 |
| EP | 0 811 843 A2 | 12/1999 |
| EP | 0 985 376 A1 | 3/2000 |
| WO | WO 01/66010 A1 | 9/2001 |
| WO | WO 02/36010 A1 | 5/2002 |
| WO | WO 03/070099 | 8/2003 |
| WO | WO 03/071940 A1 | 9/2003 |
| WO | WO 03/088835 A2 | 10/2003 |
| WO | WO 2005/018425 | 3/2005 |
| WO | WO 2005/018430 | 3/2005 |
| WO | WO 2005/018709 | 3/2005 |
| WO | WO 2005/018710 | 3/2005 |
| WO | WO 2005/018711 | 3/2005 |

OTHER PUBLICATIONS

Response filed to Office Action Summary-Non-Final Office Action dated Oct. 1, 2007, along with a Terminal Disclaimer and substitute drawing sheets filed on Feb. 7, 2008; 25 pgs.

Office Action Summary-Notice of Non-Compliant Amendment dated Feb. 27, 2008; 2 pgs.

Response filed to Office Action Summary-Notice of Non-Compliant Amendment dated Feb. 27, 2008, along with replacement sheet drawings, filed on Mar. 27, 2008, 6 pgs.

Office Action Summary-Non-Final Office Action dated Jul. 17, 2008; 6 pgs.

Response filed to Office Action Summary-Non-Final Office Action dated Jul. 17, 2008, filed on Jul. 31, 2008; 11 pgs.

Office Action Summary-Notice of Non-Compliant Amendment dated Nov. 4, 2008; 3 pgs.

Response filed to Office Action Summary-Notice of Non-Compliant Amendment dated Nov. 4, 2008, along with replacement sheet drawings, filed on Dec. 4, 2008, 38 pgs.

Office Action Summary-Final Office Action dated Mar. 10, 2009; 32 pgs.

International Search Report, Date Apr. 20, 2005 for PCT/US2004/026761; 4 pgs.

International Preliminary Report and Written Opinion, Date Mar. 2, 2006 for PCT/US2004/026761; 7 pgs.

International Search Report, Date Sep. 21, 2005 for PCT/US2004/037788; 4 pgs.

International Preliminary Report and Written Opinion, Date May 26, 2006 for PCT/US2004/037788; 12 pgs.

Office Action Summary-Non-Final Office Action dated Apr. 7, 2006; 13 pgs.

Response filed to Office Action Summary-Non-Final Office Action dated Apr. 7, 2006, filed on Jul. 6, 2006; 8 pgs.

Office Action Summary-Non-Final Office Action dated Mar. 31, 2008; 6pgs.

Response filed to Office Action Summary-Non-Final Office Action dated Mar. 31, 2008, filed on Jun. 25, 2008; 8 pgs.

Office Action Summary-Non-Final Office Action dated Sep. 3, 2008; 19 pgs.

Response filed to Office Action Summary-Non-Final Office Action dated Sep. 3, 2008, along with a Terminal Disclaimer, filed on Dec. 3, 2008; 10 pgs.

Office Action Summary-Final Office Action dated Mar. 18, 2009; 16 pgs.

International Search Report, Date Jul. 8, 2003 for PCT/US2003/005159; 6 pgs.

Written Opinion, Date Dec. 18, 2003, for PCT/US2003/005159; 4 pgs.

International Preliminary Report, Date May 7, 2004 for PCT/US2003/005159; 5 pgs.

International Search Report, Date Feb. 15, 2008 for PCT/US2005/0023155; 9 pgs.

International Preliminary Report, Date Mar. 17, 2009 for PCT/US2005/0023155; 6 pgs.

* cited by examiner

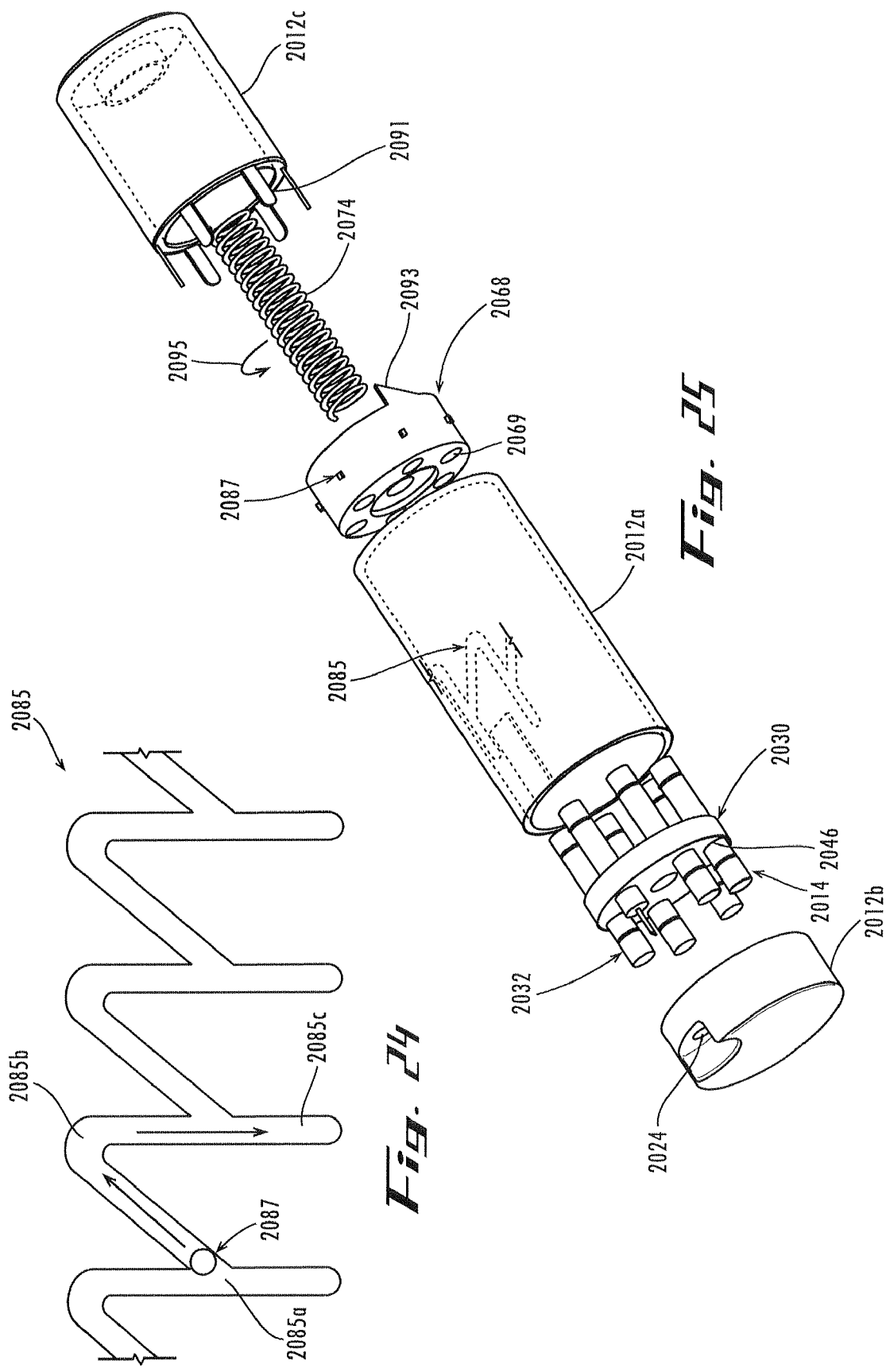

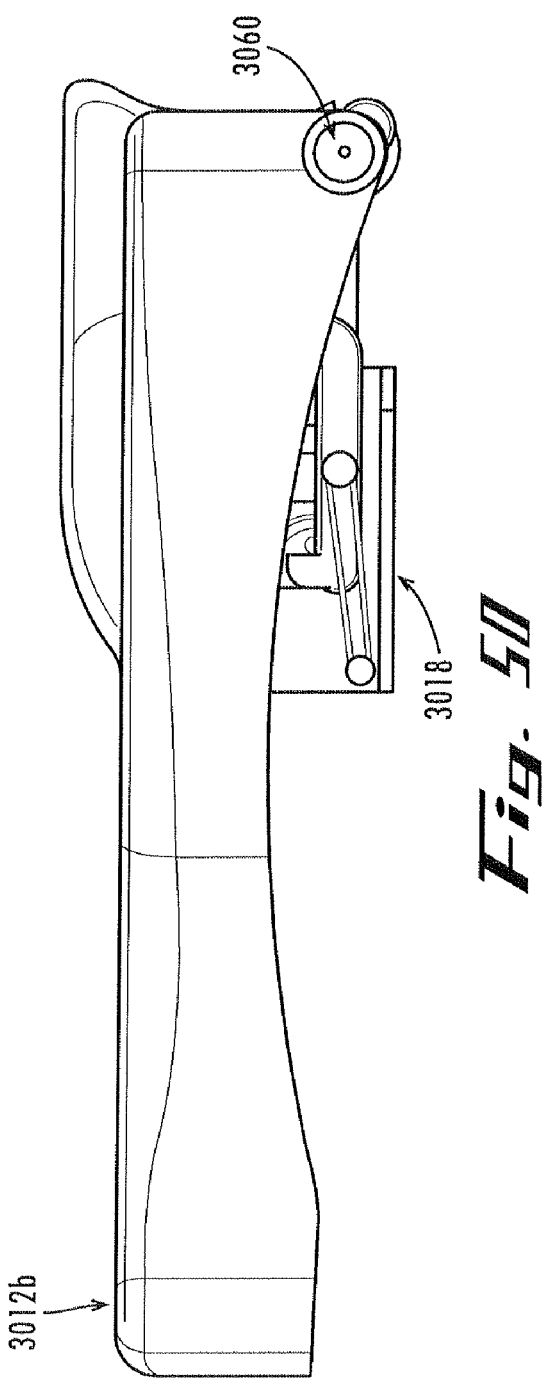
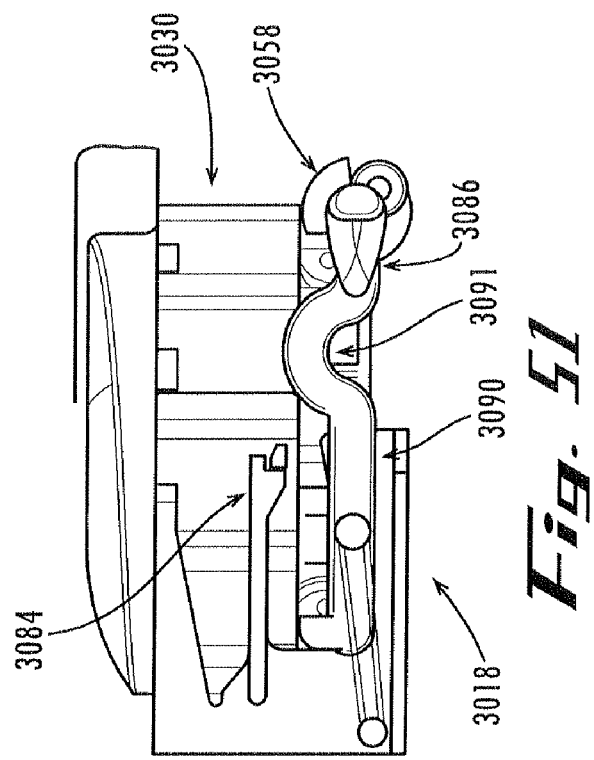

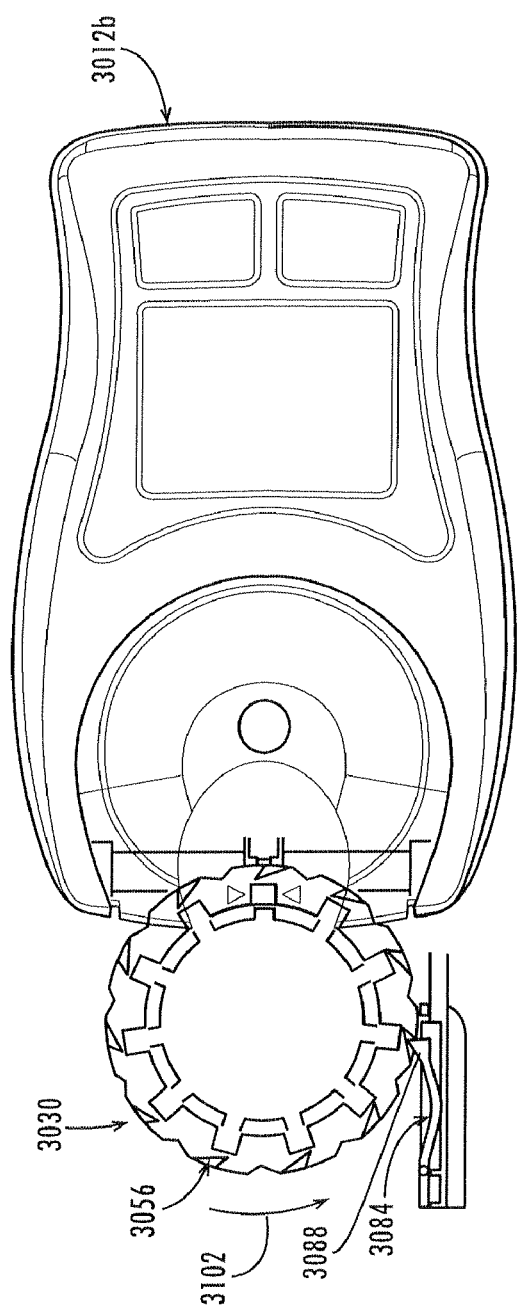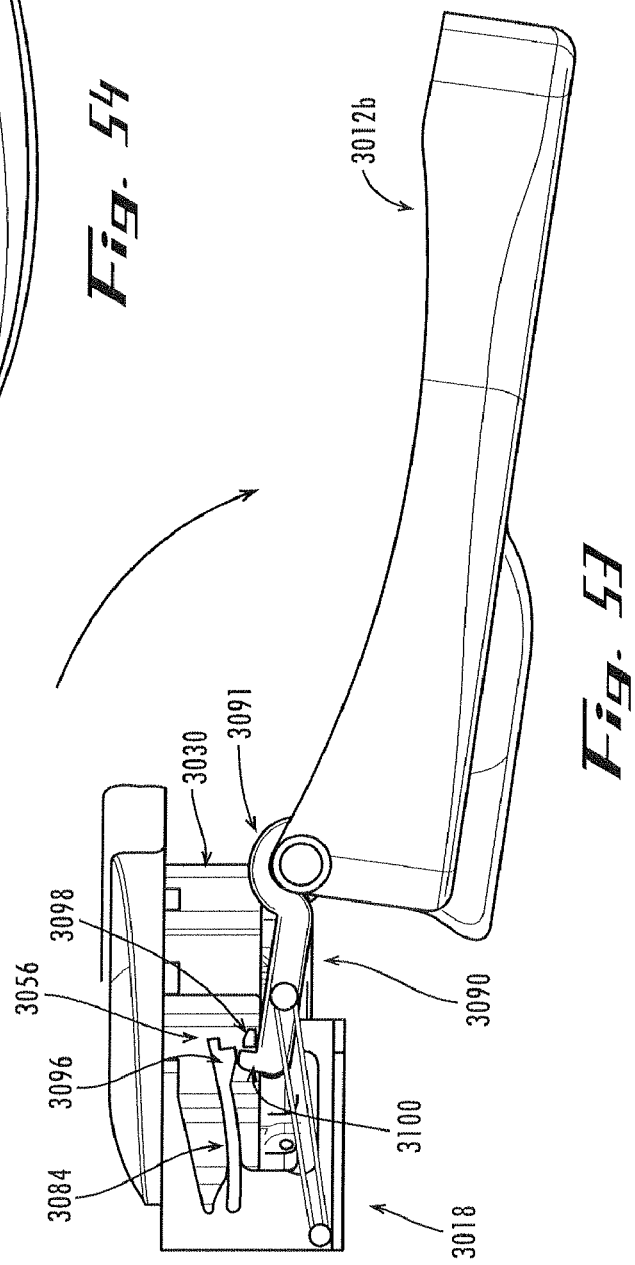

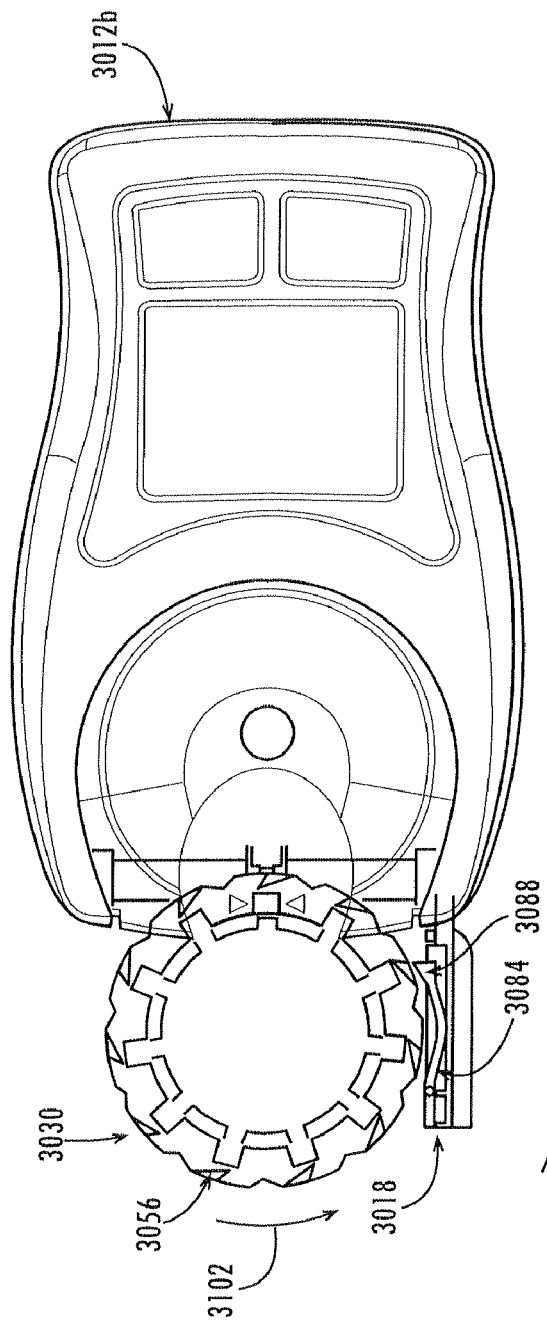
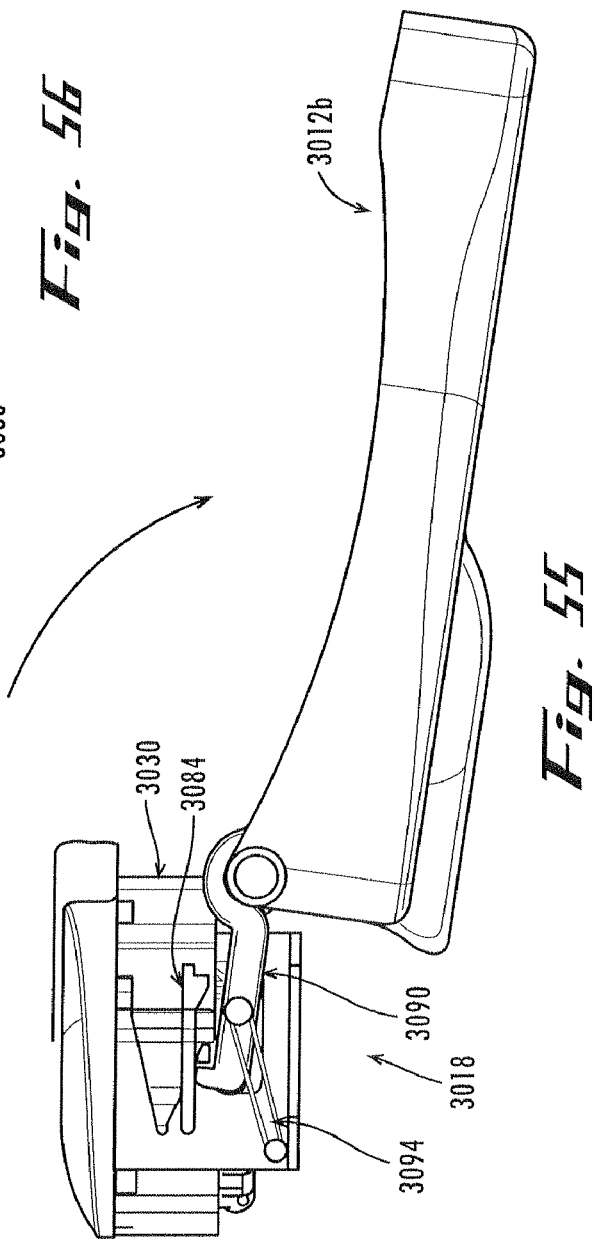
Fig. 56
Fig. 55

MULTI-LANCET DEVICE WITH STERILITY CAP REPOSITIONING MECHANISM

CROSS-REFERENCE TO RELATED APPLICATIONS

This application claims the benefit of U.S. Provisional Patent Application Ser. No. 60/598,147, filed Aug. 2, 2004, and U.S. Provisional Patent Application Ser. No. 60/497,024, filed Aug. 20, 2003, which are hereby incorporated herein by reference in their entirety.

TECHNICAL FIELD

The present invention relates generally to medical devices and procedures, and more particularly to lancing devices for the collection of samples of blood or other bodily fluid.

BACKGROUND OF THE INVENTION

Many medical procedures require puncturing of the skin, and sometimes underlying tissues, of an animal or human subject. For example, a sharp lancet tip is commonly used to puncture the subject's skin at a lancing site to obtain a sample of blood, interstitial fluid or other body fluid, as for example in blood glucose monitoring by diabetics, and in blood typing and screening applications. In some instances, a person must periodically sample their blood for multiple testing throughout the day or week. Because re-use of a lancet can result in infection or spread of bloodborne contaminants, persons requiring repeated testing often must carry multiple lancets with them. This can be inconvenient and lead to reduced compliance with a prescribed test regimen. Accordingly, it can be seen that needs exist for a convenient, compact multi-use lancing device.

Various devices are known for sampling blood and other body fluids for analysis of the condition of a human or other animal subject. For example, U.S. Pat. No. 5,971,941 is understood to show a cassette with test strips for placement by a slider. A lancet pierces the skin surface so that blood can be obtained for analysis. The lancets are integrated on a test strip, and are positioned together with the test strip. Another embodiment is understood to show a disposable cylindrical insert having a lancet and a test membrane with an aperture for the lancet. The insert is inserted in a mounting cavity of a plunger or piston, which forces the lancet outward for blood withdrawal. DE 198 19 407 A1 is understood to show a multiplicity of test strips with integrated lancets for insertion into an analysis device.

U.S. Pat. No. 4,787,398 is understood to show a device with a plunger for directing a lancet outward, and has an evaluation system and a display system. A replaceable unit is applied to the device for each measurement. The replaceable unit comprises the lancet and a test strip, which is wetted with blood. This replaceable unit is thrown away after each use. EP 0 449 525 A1 is understood to show a blood withdrawal system wherein a new lancet is inserted manually into a release device before each use. A test strip is then inserted into the device. U.S. Pat. No. 4,627,445 is understood to show a device for measuring blood sugar, with an integrated blood withdrawal unit. A new replaceable lancet and test elements must be installed to the device for testing, and afterward disassembled. U.S. Pat. No. 5,951,492 is understood to show a disposable unit with a capillary tube and a test strip, to which sampled blood taken is applied. The capillary tube includes a lancet. A new disposable unit is attached and removed before and after each measurement.

EP 0877250 A2, EP 0949506 A2 and EP 811843 A2 are understood to show devices having a multiplicity of test elements arranged on a rotatable disk carrier. The test elements are brought successively into a working position and pushed out of the housing to be wetted with blood. U.S. Pat. No. 6,228,100 and U.S. Pat. No. 4,794,926 are understood to show lancets arranged on a carrier, which is rotated with respect to a housing.

German Application DE 100 57 832 C1 is understood to show a lancing device of a known form. Other lancing devices understood to include multiple lancets are shown, for example, in U.S. patent application Ser. No. 2002/0087056 A1 and WO 02/36010 A1. EP 0589186 B1 is understood to show a lancet with a removable protective cap. WO 01/66010 A1 is understood to include a multiplicity of lancets in a magazine, with an opening of the chamber closed by an elastic material, which is penetrated in the puncture process.

Known sampling devices have, however, not proven fully satisfactory to all users for a variety of reasons. Accordingly, it is to the provision of an improved sampling device that the present invention is primarily directed.

SUMMARY OF THE INVENTION

Briefly described, example embodiments of the present invention include an improved lancing device that is convenient, compact, and includes multiple lancets in a single cassette or carousel. The present invention preferably increases convenience for the user, thereby encouraging more frequent testing and insuring compliance with the subject's prescribed testing regimen.

In one aspect, the invention is a lancet carousel for use in a multi-use lancing device. The lancet carousel includes a carrier with axial openings for receiving lancets in a parallel, coaxial arrangement. Preferably, the carrier has a recessed surface for facilitating removal and replacement of the lancet sterility caps, lateral openings for receiving a drive member to actuate the lancets, and register surfaces to facilitate advancing the carrier to move a next lancet into position for use.

In another aspect, the invention is a lancing device with a sterility cap repositioning mechanism for de-capping and re-capping the lancets. The cap repositioning mechanism includes a cap-engaging member having an opening for engaging the caps, an opening for passage of the bodies, and a channel between these opening for passage of the lancet tip. Preferably, the cap-engaging member is cooperatively coupled to a lancet advancing mechanism for sequentially advancing lancets.

In another aspect, the invention is a lancet advancing mechanism for sequentially advancing lancets into position for use within a multi-lancet device. Preferably, the advancing mechanism includes a spring-biased register that is operatively coupled to a sterility cap repositioning mechanism so that a next lancet is automatically advanced for use after a used lancet is re-capped.

Accordingly, it can be seen that the present invention provides convenient and compact multi-use lancing devices, and a lancet carousel for use therewith. The innovative features of the present invention allow the user to conveniently take multiple blood samples without the risk of infection or contamination.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 24 is an exploded view of the lancing device of FIG. 22, showing the major components of the device.

FIG. 25 is a detail view of a cam path defined by the inside surface of the housing of the lancing device of FIG. 22.

FIG. 40 is an exploded view of the drive mechanism of the lancing device of FIG. 29, showing the major components of the drive mechanism.

FIG. 50 is a side view of the lancet advancing mechanism of the lancing device of FIG. 29, showing the housing lid in the second/closed position.

FIG. 51 is a side view of the lancet advancing mechanism of FIG. 50, without the housing lid.

FIG. 53 is a side view of the lancet advancing mechanism of FIG. 50, showing the register member being released as the housing lid is rotated to the first/open position at the end of the second motion.

FIG. 54 is a plan view of the lancet advancing mechanism of FIG. 53.

FIG. 55 is a side view of the lancet advancing mechanism of FIG. 50, showing the housing lid in the first/open position and the register member advancing the carrier.

FIG. 56 is a plan view of the lancet advancing mechanism of FIG. 55.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
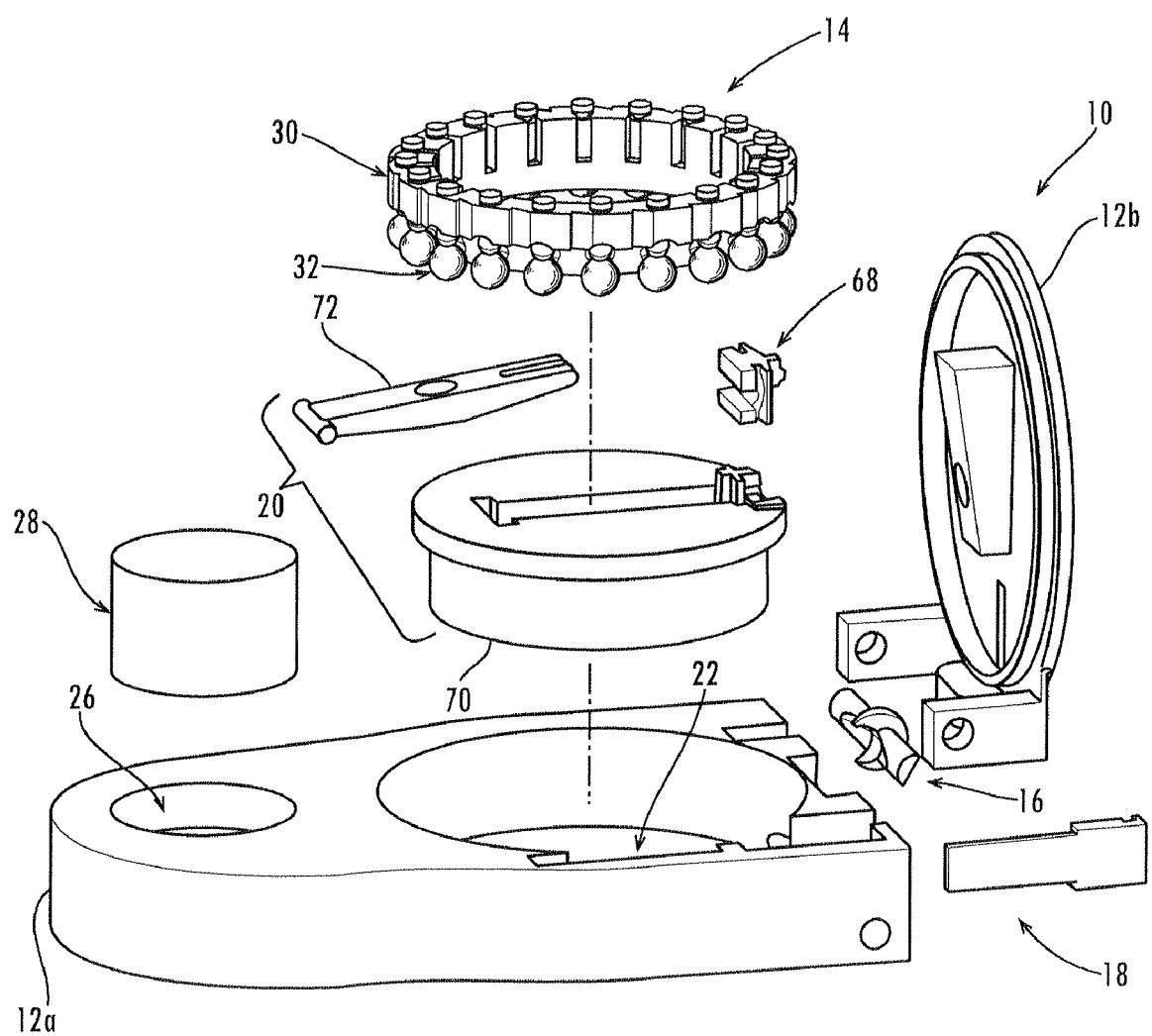
FIG. 1 is a perspective exploded view of a lancing device according to a first example embodiment of the present invention, showing a housing base and lid, a lancet carousel, a sterility cap repositioning mechanism, a lancet advancing mechanism, and a drive mechanism.
Figure 2:
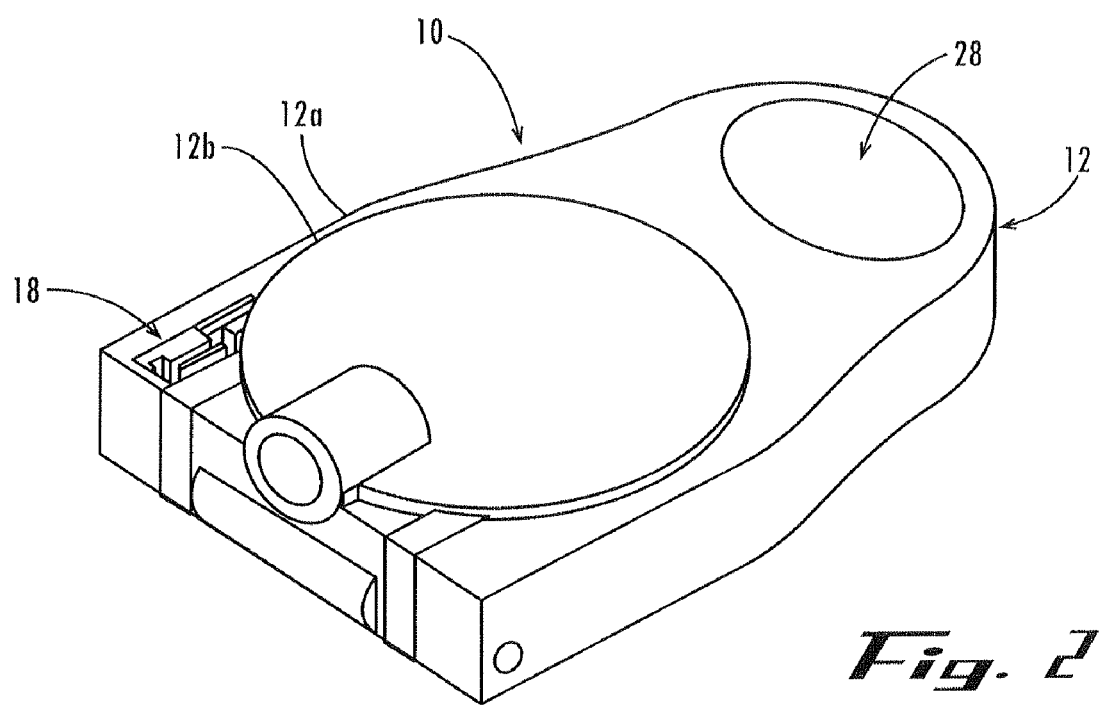
FIG. 2 is an upper perspective view of the lancing device of FIG. 1, showing the device assembled for use with the housing lid in a second/closed position.
Figure 3:
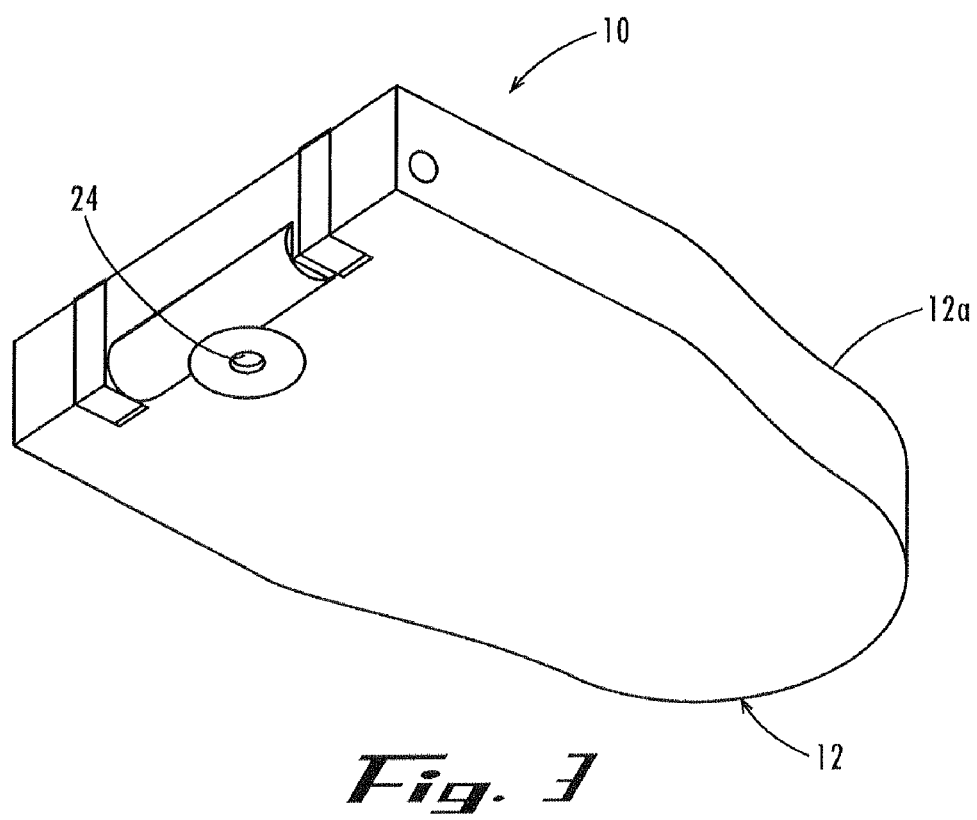
FIG. 3 is a lower perspective view of the lancing device of FIG. 2.

With reference now to FIGS. 1-18, there is shown a lancing device 10 according to a first example embodiment of the present invention. As shown in FIGS. 1-3, the lancing device 10 includes a reusable housing 12, a lancet carousel 14, a sterility cap repositioning mechanism 16, a lancet advancing mechanism 18, and a drive mechanism 20. Most of these components can be made of molded plastic for economy. The housing 12 has a first section and a second section that is removable for loading and removing the lancet carousel 14. For example, the housing 12 may include a first section base 12a and a second section lid 12b that is hinged to the base. The housing 12 has a chamber 22 for the lancet carousel 14 and an opening 24 for the lancet tips to extend through to lance the user's skin. In addition, the housing 12 may include a mounting structure for a blood testing device for use with the blood samples obtained when using the lancing device 10. For example, the housing 12 may include a chamber 26 for a conventional blood meter 28, with the lancing device 10 sold with the blood meter or separately.

Figure 4:
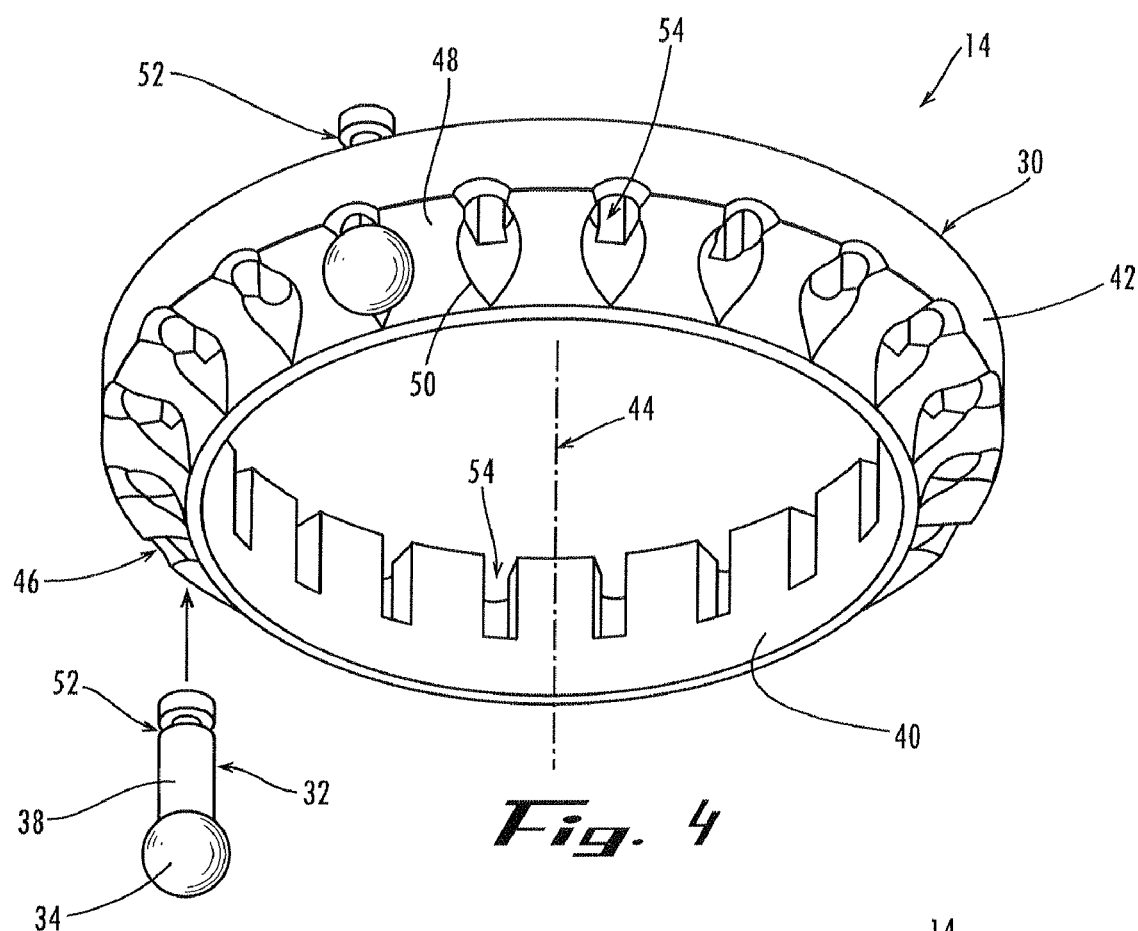
FIG. 4 is a lower perspective view of the lancet carousel of FIG. 3, showing a carrier and a lancet being loaded into the carrier body-first.
Figure 5:
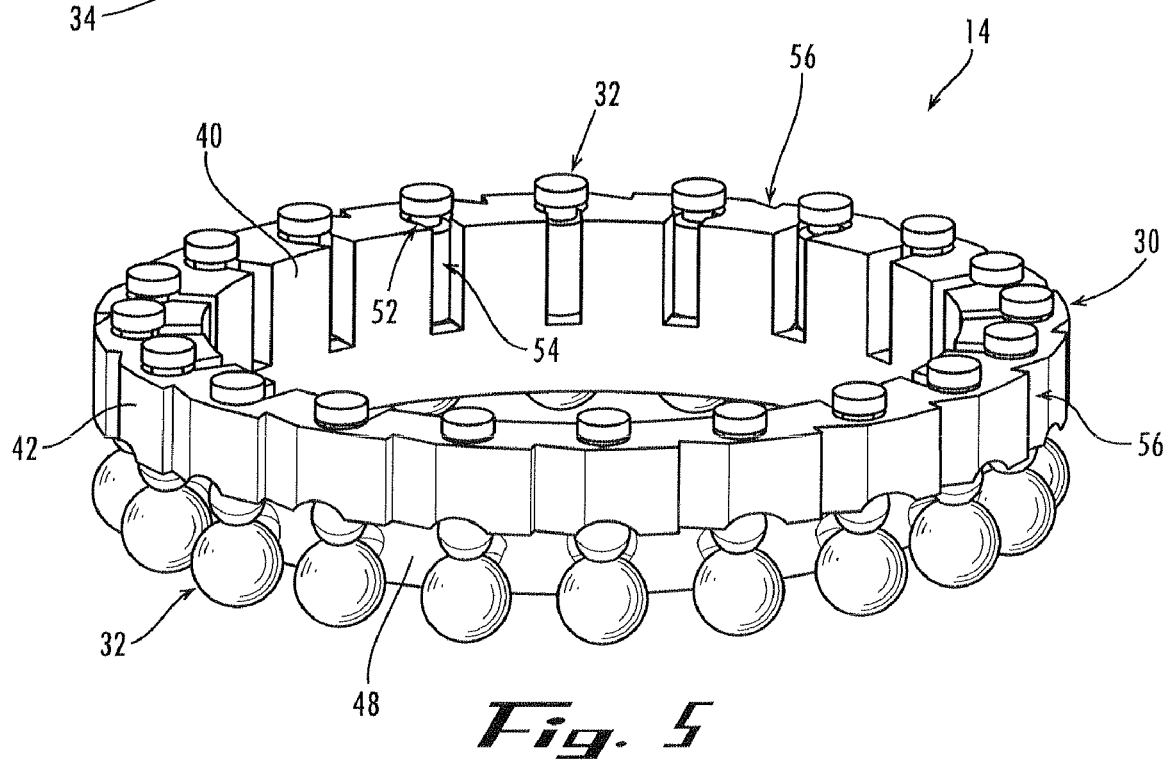
FIG. 5 is an upper perspective view of the lancet carousel of FIG. 1, showing the carrier fully loaded with lancets.

FIGS. 4 and 5 show the lancet carousel 14, which includes a carrier 30 and at least one and preferably a plurality of lancets 32. The exact number of lancets 32 that the carrier 30 holds is selected depending on space and use needs, and can vary widely. The lancets 32 each have a sterility cap 34 protecting a lancet tip 36 (see FIGS. 6 and 7) that is held by a lancet body 38. The lancet tip 36 may be any structure for lancing skin, for example, a needle or a blade. The lancets 32 are driven through a lancing stroke from a retracted position within the housing 12 to an extended position with the lancet tip 36 of an active lancet extending outwardly of the housing through the lancing opening 24 to pierce the skin of a human or animal subject at a lancing site.

The carrier 30 of the lancet carousel 14 may be cylindrical, or it may be polygonal or have another regular or irregular shape. Also, the carrier 30 is sized, shaped, and constructed for removable insertion into the chamber 22 of the housing 12. In this way, after all of the lancets 32 on the carrier 30 have been used, the user can remove the spent carrier for disposal and then load a new one full of lancets. Preferably, the carrier 30 is annular-shaped and has an inner surface 40, an outer surface 42, and an axis 44. Alternatively, the carrier 30 may be provided with different geometry.

The carrier 30 has a plurality of lancet openings 46 sized and shaped for receiving the lancets 32 with a free-floating fit. That is, the openings 46 are configured so that the lancets 32 can longitudinally slide freely within the openings during the lancing operation, with negligible frictional resistance to movement. In addition, the lancet openings 46 are configured in a parallel arrangement so that the lancets 32 are held by the carrier 30 in a parallel arrangement. Preferably, the lancet openings 46 and the lancets 32 are coaxially arranged relative to the axis 44 of the annular carrier 30, as shown with particularity in FIG. 4.

Preferably, the carrier 30 has a circumferential recessed surface 48 through which the coaxial lancet openings 46 extend. With the carrier 30 being annular-shaped, a teardrop-shaped rim 50 is formed where each of the lancet openings 46 extends through the recessed surface 48, as shown with particularity in FIG. 4. In this configuration, the lancet openings 46 receive the lancet bodies 38 and the recessed surface 48 receives the sterility caps, while leaving the sterility caps exposed for engagement by a cap-engaging member that repositions the sterility caps, as described herein.

In addition, the lancets 32 each have a drive surface 52 for engagement with a drive member to propel the lancets, as described herein. The lancet drive surface 52 is preferably provided by a notch in each lancet body 38. Alternatively, the drive surface 52 may be the tail end (opposite the sterility cap) of the lancet body or another surface defined on the lancet. The lancets 32 are preferably arranged with the drive surfaces 52 extending out of the carrier 30, as shown, so that the drive member can be moved laterally from engagement with one lancet to another one.

Also, the carrier 30 has a plurality of lateral openings 54 that each extend between the inner surface 40 and one of the lancet openings 46. The lateral openings 54 are configured to receive the drive member through them in the direction of the lancing stroke so that the drive member can engage the lancet drive surface 52 through the travel of the lancet during the lancing stroke.

Furthermore, the carrier 30 has a plurality of register surfaces 56 (see FIG. 5), with each one of the register surfaces indexed to a corresponding one of the lancet openings 46. Preferably, the register surfaces 56 are provided by ramped notches in the outer surface 42 of the carrier 30, as shown. Alternatively, the register surfaces 56 may be provided by tabs or arms extending from the carrier, recessed catch surfaces in another wall of the carrier, or otherwise. The register surfaces 56 are sequentially engaged by a register member to advance the carrier 30, as described herein. Because of the indexing, for example, one register surface 56 per lancet opening 46, the register surfaces 56 advance the carrier 30 from a first position with one of the lancets 32 engaged by the drive member to a second position with a next one of the lancets engaged by the drive member.

In order to save space, the lancet bodies 38 are kept relatively small. The sterility caps 34 are a little larger in order to make it easy enough to remove the sterility caps 34 to expose the lancet tip 36 for use. That is, the sterility caps 34 preferably have a larger axial profile than the lancet bodies 38. Thus, the lancet bodies 38 slide into the lancet openings 46, but the sterility caps 34 are too large to be received in the lancet openings.

In this configuration, the lancets 32 are loaded into the carrier 30 by grasping a first one of the lancets 32 and inserting it into a first one of the lancet openings 46 in a body-first orientation. The lancets 32 are preferably inserted linearly into the openings 46. Alternatively, the lateral openings 54 may be larger and the lancets 32 inserted at an angle through the lateral openings and then tilted to their coaxial orientation. Or the lancet bodies 38 may have tail-end retainer flanges that are larger than the lancet openings 46 and caps 34 that are smaller, so that the lancets 32 are loaded cap-first into the carrier 30. In any event, the first lancet 32 is then positioned so that its lancet body 38 is in the lancet opening 46, its drive surface 52 is exposed for engagement by the drive member, and its sterility cap 34 is exposed for de-capping. This process is then repeated for each lancet 32 until the carrier 30 is full.

In addition, because the lancets 32 preferably free-float within the lancet openings 46, they could slide out inadvertently. Therefore, the lancet loading process may include restraining the lancets 32 in the openings 46 during and/or after the loading process so that they do not fall out of the carrier 30. For example, the lancets 32 may be restrained by applying a cover and/or adhesive layer to the carrier 30 adjacent a tail end of the lancets to retain them in their corresponding openings 46.

Referring now to FIGS. 6-11, 17, and 18, the structure of the sterility cap repositioning mechanism 16 will now be described in conjunction with an example method of operation of the sterility cap repositioning mechanism 16 to de-cap and re-cap the lancets. The sterility cap repositioning mechanism 16 is described and shown herein with reference to the multi-lancet lancing device 10 using a lancet carousel 14 for illustration purposes only. Thus, the mechanism 16 can be used in other multi-lancet devices, or even adapted for use with single-use disposable lancets (without an advancing mechanism), if so desired.

The sterility cap repositioning mechanism 16 includes a cap-engaging member 58 that is movably coupled to the housing 12. For example, the cap-engaging member 58 may be rotationally coupled to the housing 12 by an axle 60. The cap-engaging member 58 is operated by an actuating member. For example, the axle 60 may be keyed to the housing lid 12b so that they move together, whereby the housing lid serves as the actuating member in addition to covering the lancet-holding chamber 22. The housing lid 12b may be provided with a gripping surface or member, if desired, to make it easy to grasp for opening and closing.

The cap-engaging member 58 has a cap opening 62, a body opening 64, and a channel 66 between the cap opening and the body opening. The cap opening 62 is configured to eccentrically receive and engage the sterility caps 34 when the cap-engaging member 58 is rotated from a first position through a first motion. The channel 66 is configured to receive the lancet tips 36 through it when the cap-engaging member 58 is rotated through the first motion. And the body opening 64 is configured to receive the lancet bodies 38 through it free-floatingly when, with the cap-engaging member 58 rotated to a second position at the end of the first motion, the lancing device 10 is actuated.

Preferably, the cap opening 62, the body opening 64, and the channel 66 are curved, for example, they have semicircular profiles formed in a spherical body for use with lancets 32 having cylindrical bodies and spherical caps, as is shown. Alternatively, the cap opening 62 and the body opening 64 may have profiles that are rectangular or have another regular or irregular shape. Also, the cap opening 62 and the body opening 64 may intersect with each other making the channel 66 effectively a part of the body opening, or the channel 66 may be sized and shaped similarly to the body opening 64, but these configurations leave less surface area in the cap opening for engaging and removing the caps 34.

Figure 6:
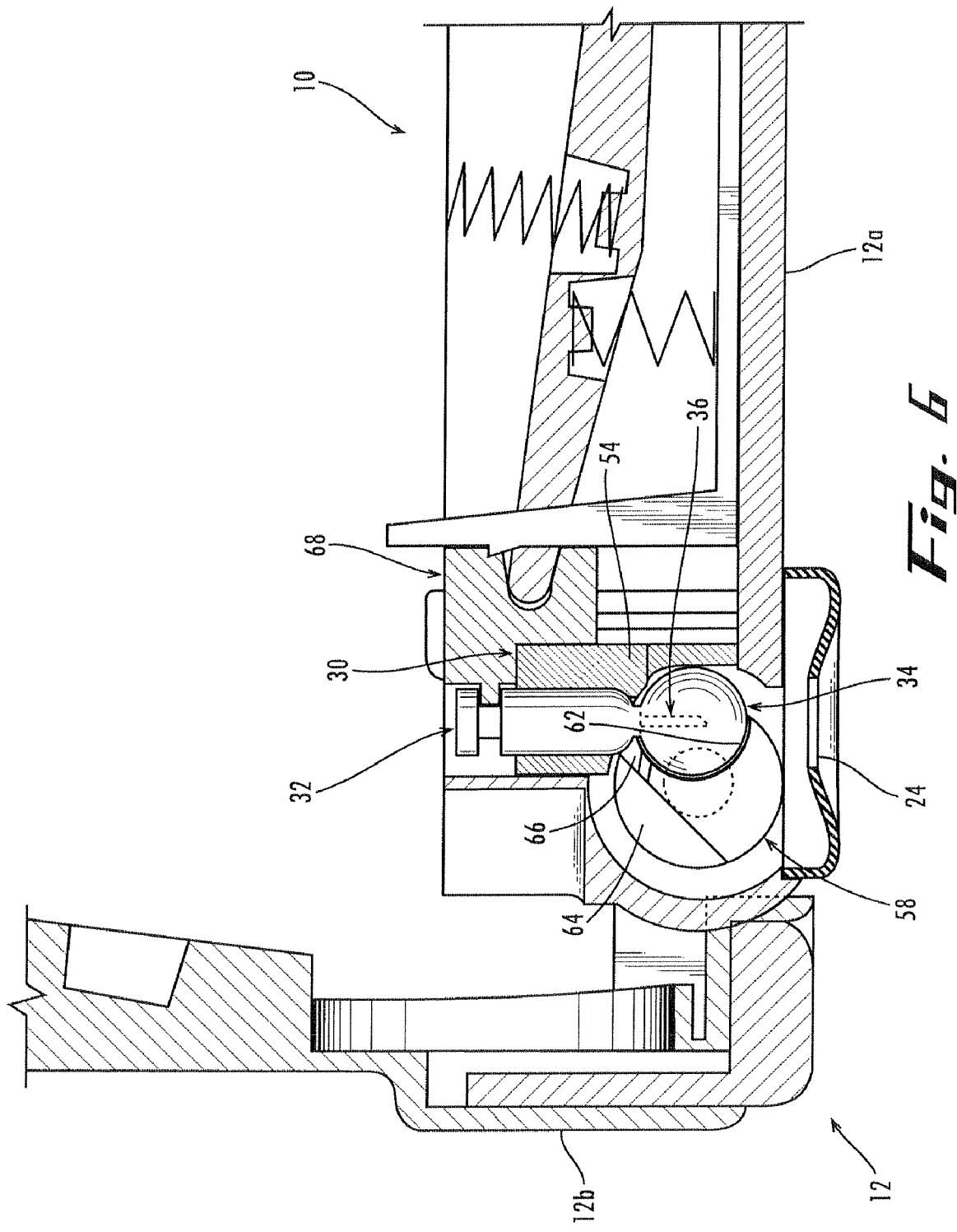
FIG. 6 is a cross-sectional side view of a portion of the lancing device of FIG. 1, showing a first one of the lancets in a set position, the housing lid in a first/open position, and a cap-engaging member of the sterility cap repositioning mechanism in a first position.

FIG. 6 shows the lancing device 10 with a first one of the lancets 32 in a set position, with the sterility cap 34 between the lancet tip 36 and the housing opening 24, and engaged by the drive member 68. The housing lid 12b is in the first/open position and the cap-engaging member 58 is in the first/capped position adjacent the sterility cap. The lancet carousel 14 may be provided with a dummy lancet (without a lancet tip or sterility cap) for initial engagement by the cap-engaging member 58, which would eliminate any clearance problems with inserting the carousel into the housing with one of the caps engaged with the cap-engaging member 58. To begin the de-capping process, the user operates the actuating member (the housing lid 12b in this embodiment).

Figure 7:
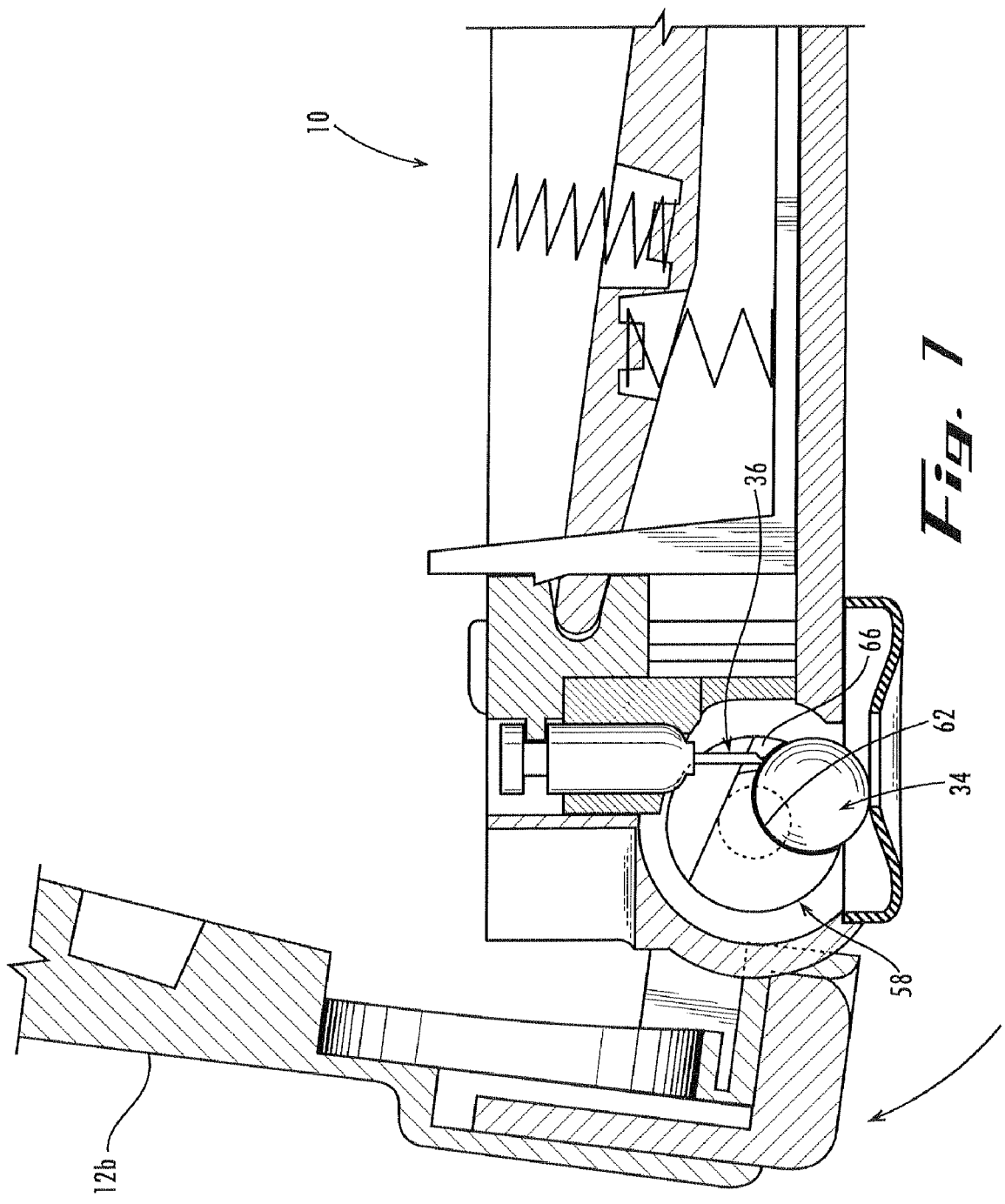
FIG. 7 is a cross-sectional side view of the portion of the lancing device of FIG. 6, showing the housing lid being rotated to rotate the cap-engaging member through a first motion to remove the sterility cap from the lancet tip.

FIG. 7 shows the housing lid 12b being rotated to rotate the cap-engaging member 58 through the first motion. In the first motion, the cap opening 62 receives the sterility cap 34 and pulls it off of the lancet tip 36 as the cap-engaging member 58 rotates. The channel 66 receives the lancet tip 36 during this motion to eliminate interference and permit the cap-engaging member 58 to rotate past the lancet tip.

Figure 8:
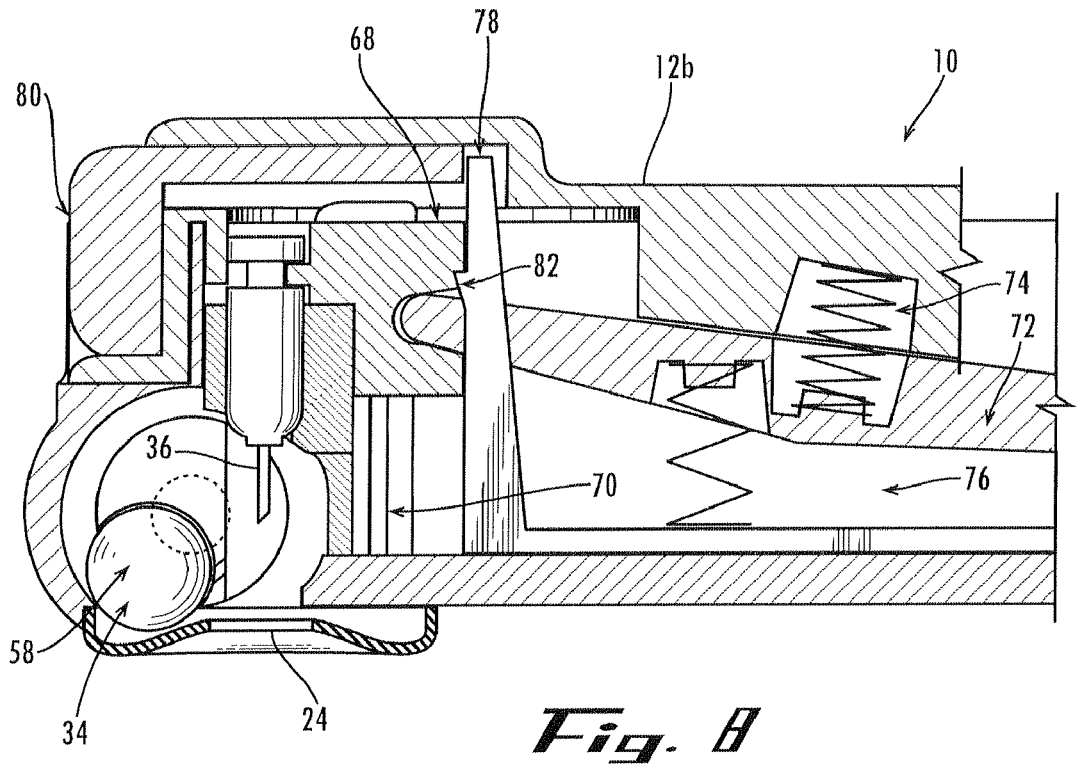
FIG. 8 is a cross-sectional side view of the portion of the lancing device of FIG. 6, showing the housing lid in the second/closed position and the cap-engaging member in a second position with the cap clear of the housing opening.

FIG. 8 shows the housing lid 12b rotated to the second/closed position and the cap-engaging member 58 rotated to the second position. In this position, the cap-engaging member 58 has rotated the sterility cap 34 off of the lancet tip 36 to a position clear of the housing opening 24. Preferably, the cap-engaging member 58 in the second position retains the sterility cap 34 within the housing, as shown, so the cap can be replaced on the lancet tip 36 after the skin is lanced. The lancing device 10 is now ready to be actuated, by operation of the drive mechanism 20, to lance the user's skin.

The drive mechanism 20 includes a frame 70 for a spring arm 72 that is biased by a drive spring 74 and a return spring 76, with the spring arm pivotally engaging the drive member 68 (see also FIG. 1). When the housing lid 12b is moved to the second/closed position, it compresses and charges the drive spring 74 against the spring arm 72, thereby charging the drive member 68. The spring arm 72 pivots relative to the drive member 68 by a tongue and recess structure as shown, by a pivot pin and slot, or otherwise. The springs 74 and 76 may be held in place by recesses as shown or otherwise, and other types, lengths, and configurations of springs may be provided. The drive mechanism 20 further includes a releasable catch member 78 that releasably engages the drive member 68, and a drive actuating member 80 that the user presses or otherwise moves to release the catch member 78 from the drive member 68. The catch member 78 may releasably engage the drive member 68 by, for example, the ramp-and-notch structures 82 shown.

Figure 9:
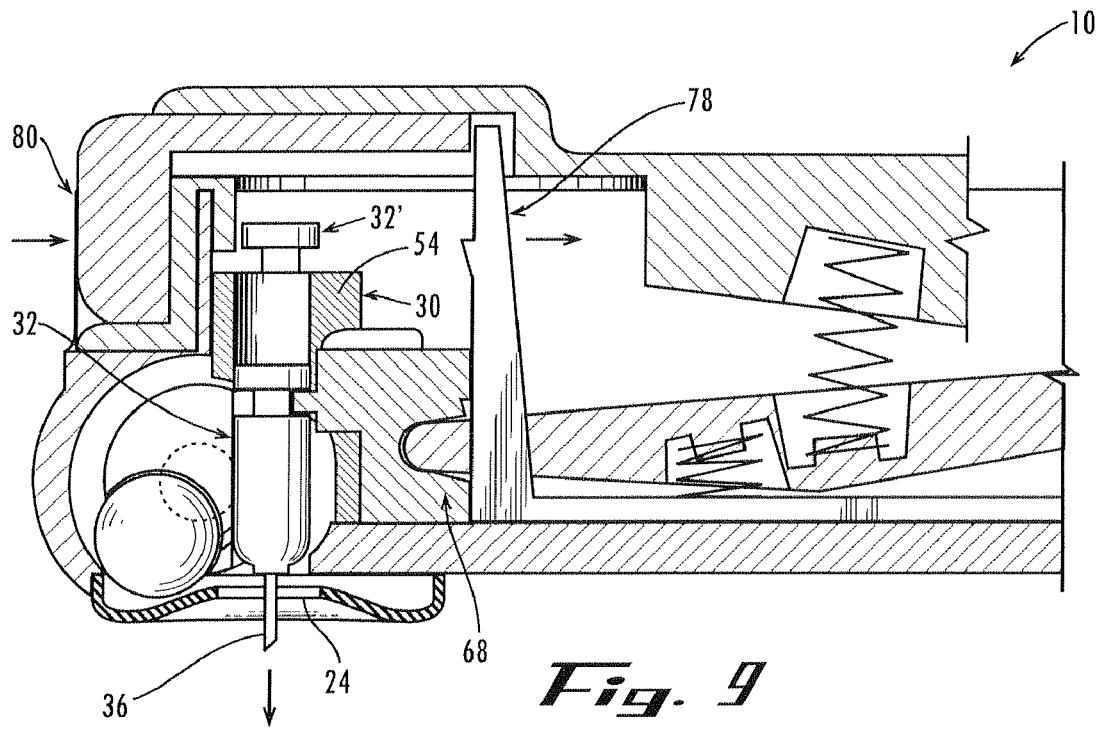
FIG. 9 is a cross-sectional side view of the portion of the lancing device of FIG. 6, showing the drive mechanism being actuated to launch the lancet.
Figure 17:
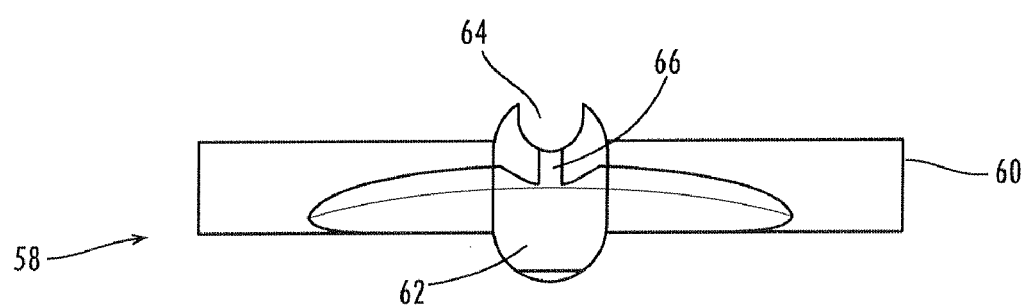
FIG. 17 is a bottom side view of the cap-engaging member of the sterility cap repositioning mechanism of FIG. 1 when in the position of FIGS. 8 and 9.
Figure 18:
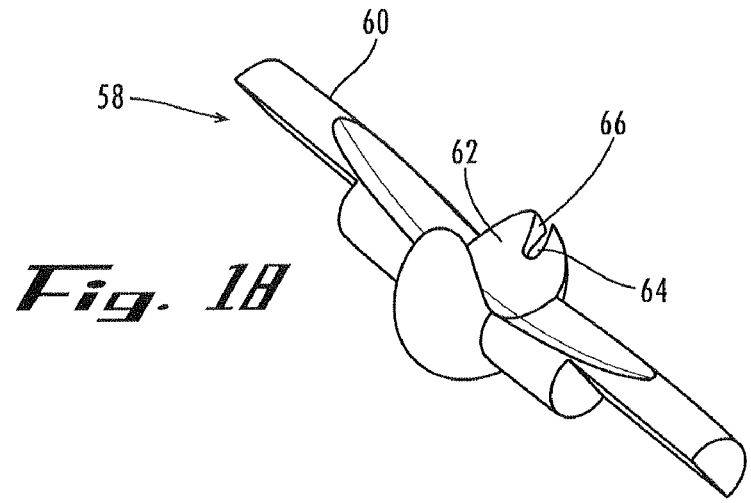
FIG. 18 is a perspective view of the cap-engaging member of the sterility cap repositioning mechanism of FIG. 1.

FIG. 9 shows the drive mechanism 20 being actuated to launch the lancet 32. The user presses the drive actuating member 80 (in the direction of the adjacent arrow), which pushes back the releasable catch member 78 (in the direction of the adjacent arrow) from engagement with the drive member 68. A drive surface 67, preferably on a drive arm or other protrusion, of the drive member 68 engages the drive surface 52 of the lancet 32, so that movement of the drive member produces movement of the lancet. Then the drive member 68, charged by the drive spring 74, launches the lancet 32 (in the direction of the adjacent arrow). The lancet body 38 passes through the body opening 64 of the cap-engaging member 58, which when viewed from the bottom now appears as shown in FIG. 17.

At its fully extended position, the lancet tip 36 extends through the housing opening 24 to lance the user's skin. The return spring 76 is now compressed and charged, ready to retract the drive member 68 and thus the lancet 32 back safely into the housing so that the next lancet 32' can be advanced into engagement with the drive member 68 for use.

Figure 10:
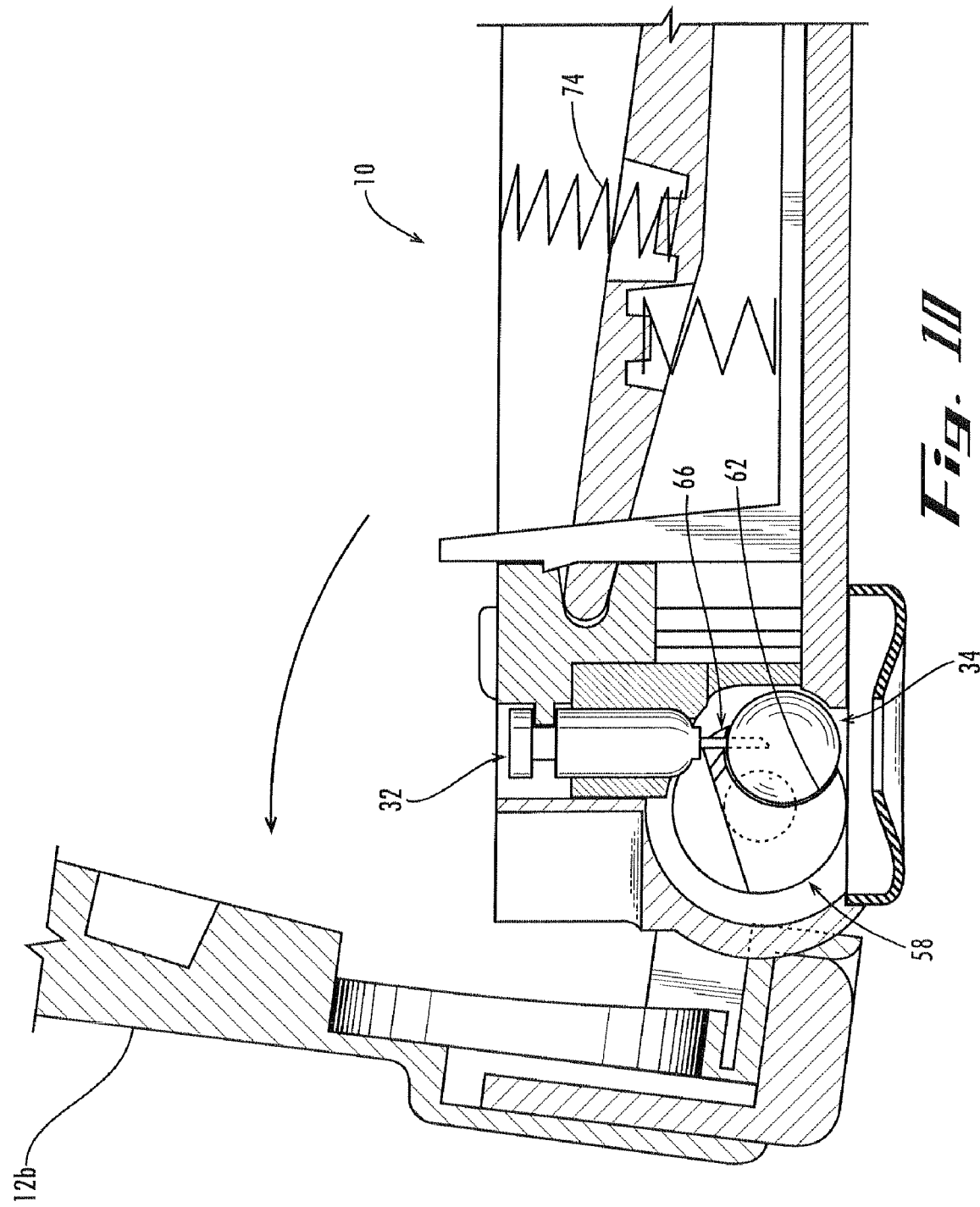
FIG. 10 is a cross-sectional side view of the portion of the lancing device of FIG. 6, showing the housing lid and the cap-engaging member being rotated through a second motion to replace the sterility cap on the lancet and return the lancet to the set position.

FIG. 10 shows the housing lid 12b being rotated to rotate the cap-engaging member 58 from the second position, through the second motion, and back to the first position. In the second motion, the cap-engaging member 58 rotates to place the sterility cap 34 on the lancet tip 36. In this embodiment, the cap repositioning mechanism 16 is configured to replace the sterility cap 34 on the lancet tip 36 that it was previously removed from. In addition, as the cap-engaging member 58 pushes the cap 34 back onto the lancet tip 36, it pushes the entire lancet 32 back to the set position. In this embodiment, the drive spring 74 is not charged by this motion because the housing lid is being rotated away out of engagement with the drive spring.

Figure 11:
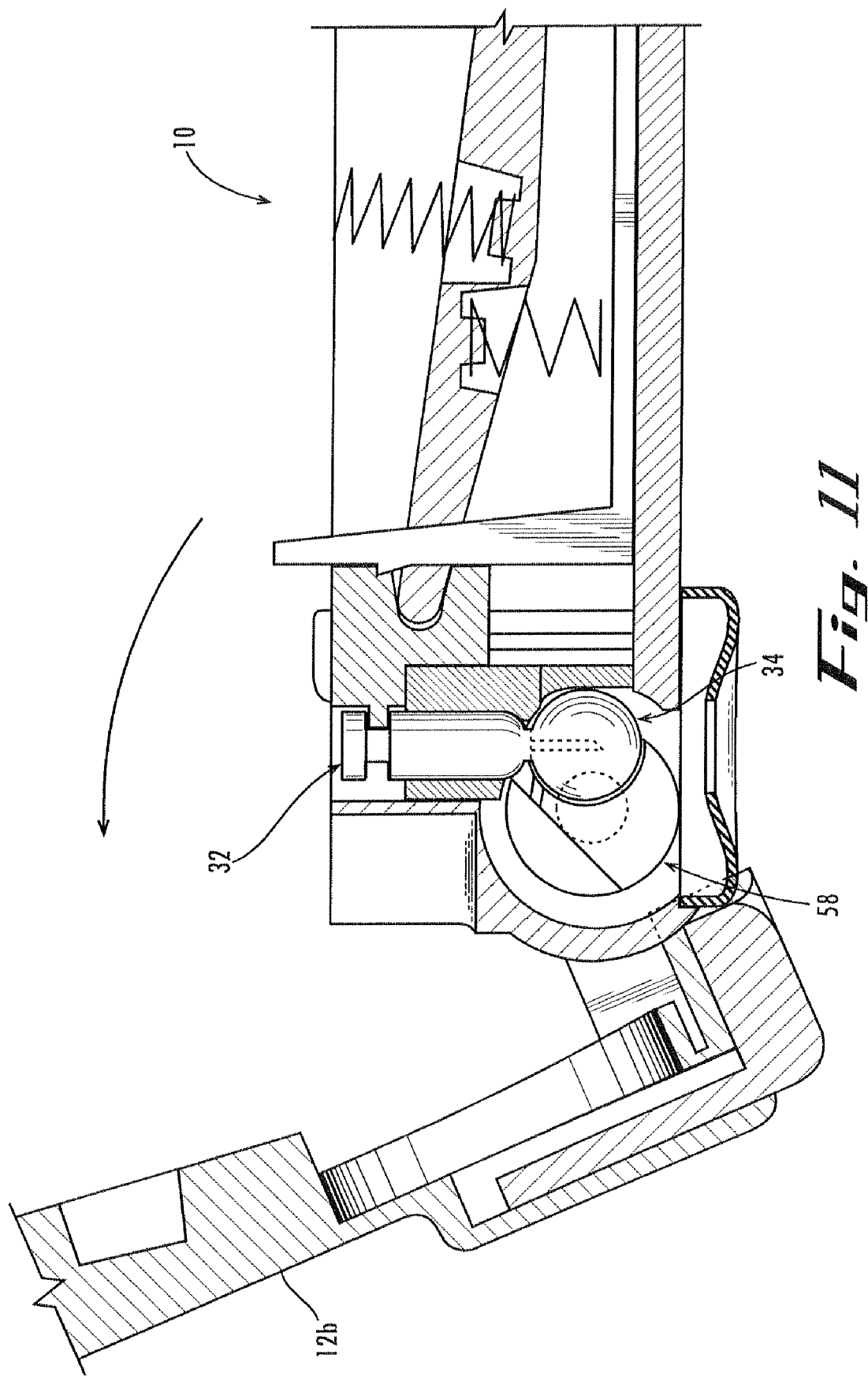
FIG. 11 is a cross-sectional side view of the portion of the lancing device of FIG. 6, showing the housing lid rotated back to the first/open position and the cap-engaging member rotated back to the first position with the cap replaced on the lancet.

FIG. 11 shows the housing lid 12b rotated back to the first/open position and the cap-engaging member 58 rotated back to the first position with the cap 34 replaced on the lancet 32. Now the spent lancet 32 is advanced and the next lancet on the carrier 30 is advanced into the set position of FIG. 6, and the process is repeated until the lancet carousel 14 is spent.

Once the lancet carousel 14 is spent, the user can open the housing lid 12b, remove the spent lancet carousel 14, install a new lancet carousel, and close the lid for further use.

Referring now to FIGS. 12-16, the structure of the lancet advancing mechanism 18 will now be described in conjunction with an example method of operation of the lancet advancing mechanism 18 to advance lancets in a lancet carrier. The lancet advancing mechanism 18 is described and shown herein with reference to the multi-lancet lancing device 10 using a lancet carousel 14 for illustration purposes only. Thus, the mechanism 18 can be readily adapted for use with other multi-lancet lancing devices and lancet carousels, including disposable lancing devices if so desired.

Figure 12:
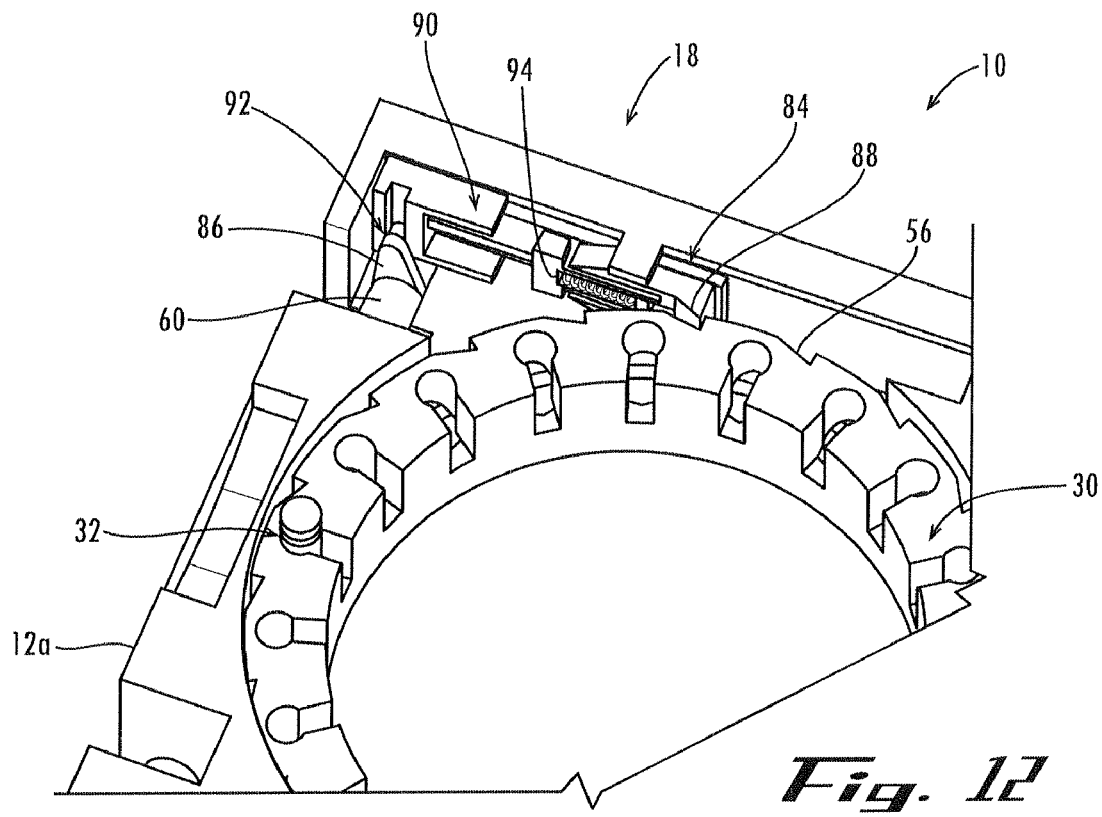
FIG. 12 is a perspective view of a portion of the lancing device of FIG. 1, showing a lancet register member of the lancet advancing mechanism when the housing lid and cap-engaging member are in the second/closed position of FIG. 8.

FIG. 12 shows the position of the lancet register member 84 when the housing lid and cap-engaging member are in the second/closed position of FIG. 8. The lancet register member 84 is preferably operably coupled to the cap-engaging member 58 so that the sterility cap repositioning mechanism 16 and the lancet advancing mechanism 18 are operated together by the same actuating member, which is the housing lid in this embodiment. For example, the lancet advancing mechanism 18 may be coupled to the axle 60 of the cap-engaging member 58. In this embodiment, a direction-reversing linkage (not shown) is provided so that when the cap-engaging member 58 rotates on one direction an advancing arm 86 of the lancet advancing mechanism 18 rotates in the opposite direction. Alternatively, the lancet advancing mechanism 18 may be readily adapted to eliminate the direction-reversing linkage, as would be understood by a person of ordinary skill in the art.

The lancet register member 84 engages and advances the carrier 30 to sequentially move the lancets 32 into the set position for use. Thus, the lancet register member 84 is configured to advance a first lancet out of engagement with the drive member and to advance a second lancet into engagement with the drive member during the second motion after the first lancet has been re-capped and reset. Preferably, the register member 84 includes a ramp 88 that releasably engages the preferred ramp-notched register surfaces 56 of the carrier 30.

Figure 13:
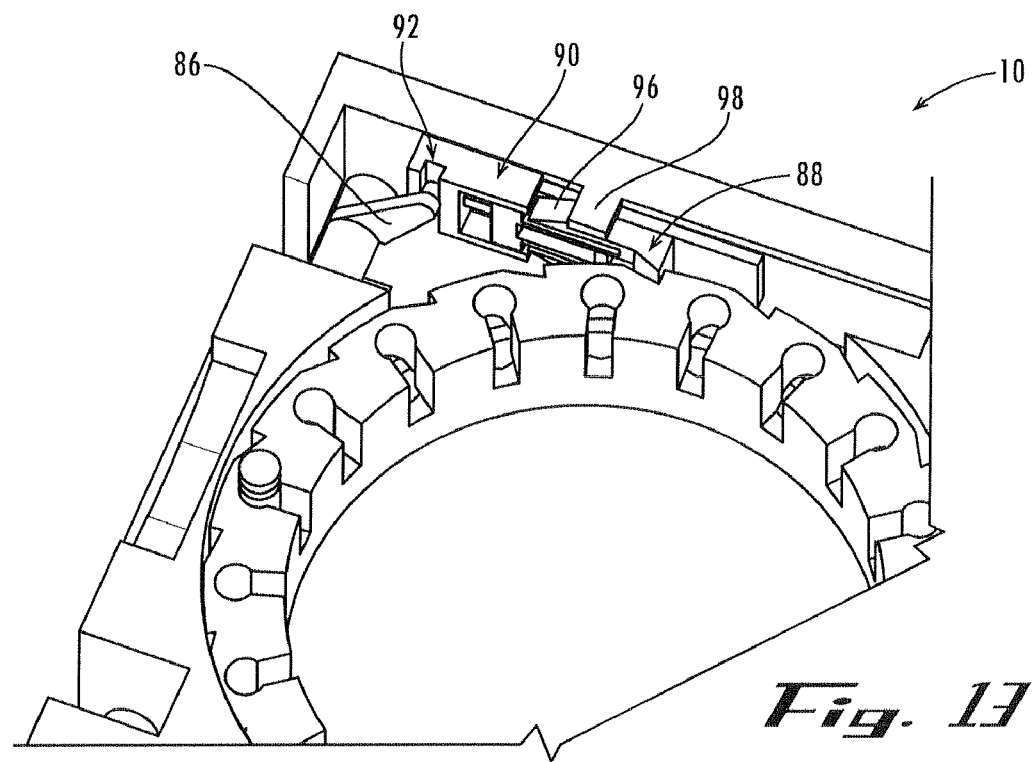
FIG. 13 is a perspective view of the portion of the lancing device of FIG. 12, showing the register member being charged as the housing lid and cap-engaging member are rotated through the second motion.

FIG. 13 shows the register member 84 being charged as the housing lid and cap-engaging member are rotated through the second motion (see FIG. 10). The lancet advancing mechanism 18 further includes an advancing slide member 90 that is coupled to the advancing arm 86 so that rotation of the advancing arm produces lateral movement of the slide member. For example, the slide member 90 and the advancing arm 86 may be coupled together by a pin-and-groove structure 92 as shown. As the slide member 90 is moved towards the register member 84, an advancing spring 94 (see FIG. 12) is compressed and charged. The register member 84 is retained in position to charge the spring 94 by a ramped engagement member 96 that in turn is retained in position by a catch member 98.

Figure 14:
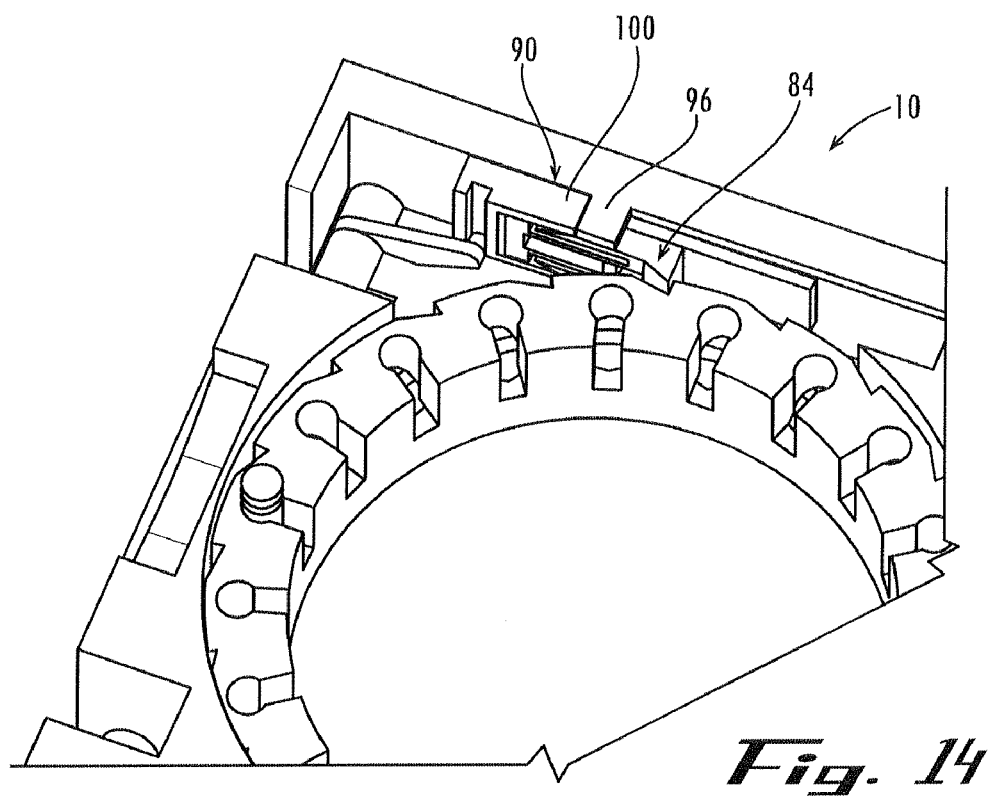
FIG. 14 is a perspective view of the portion of the lancing device of FIG. 12, showing the register member being released as the housing lid and cap-engaging member are rotated through the second motion.
Figure 15:
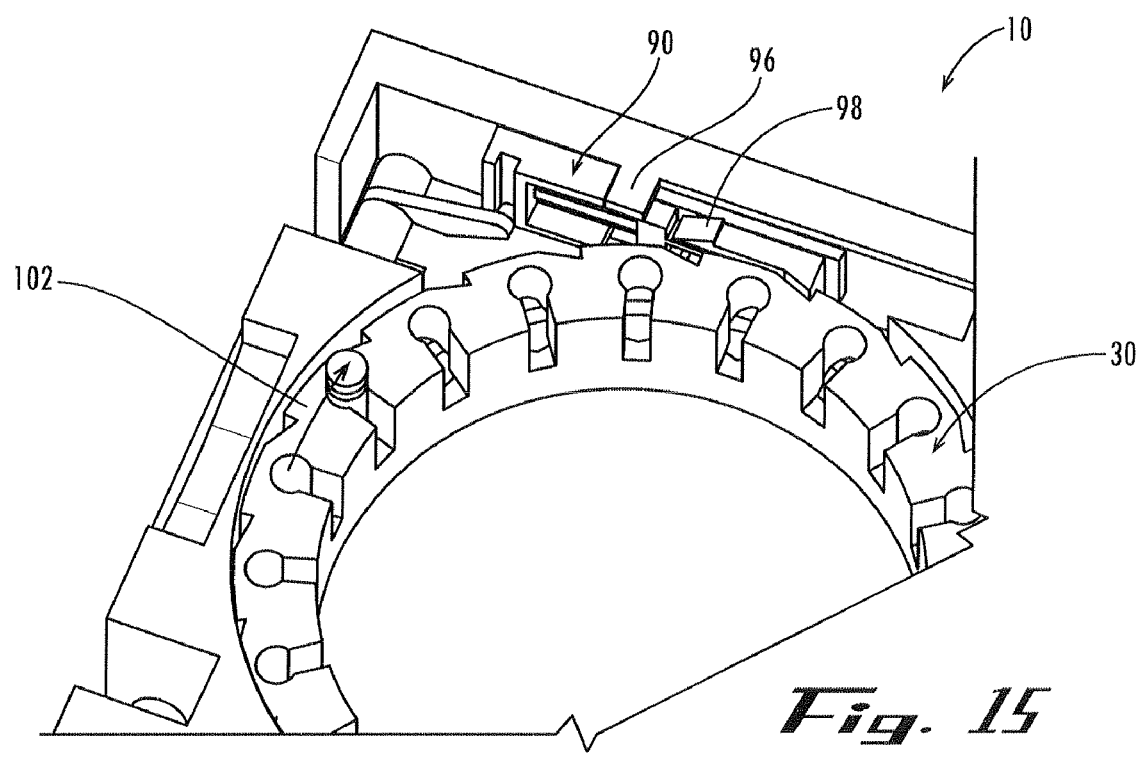
FIG. 15 is a perspective view of the portion of the lancing device of FIG. 12, showing the register member moved to advance the lancet carrier by one lancet with the housing lid and cap-engaging member in the first/open position of FIGS. 6 and 11.

FIGS. 14 and 15 show the register member 84 being released as the housing lid and cap-engaging member are rotated through the end of the second motion (see FIGS. 6 and 11). The slide member 90 includes an advancing release member 100 that engages and releases the ramped engagement member 96 so that it can move past the catch member 98. In this embodiment, as the release member 100 advances, it slides along the ramped engagement member 96, as shown in FIG. 14. This causes the ramped engagement member 96 to deflect, which releases the register member 84 to shoot past the catch member 98 by the charged spring 94 to the position shown in FIG. 15. This movement by the register member 84 rotates the carrier 30 (in the direction of arrow 102) by one lancet position, so that the next lancet is now in the set position, engaged by the drive member and ready for use.

Figure 16:
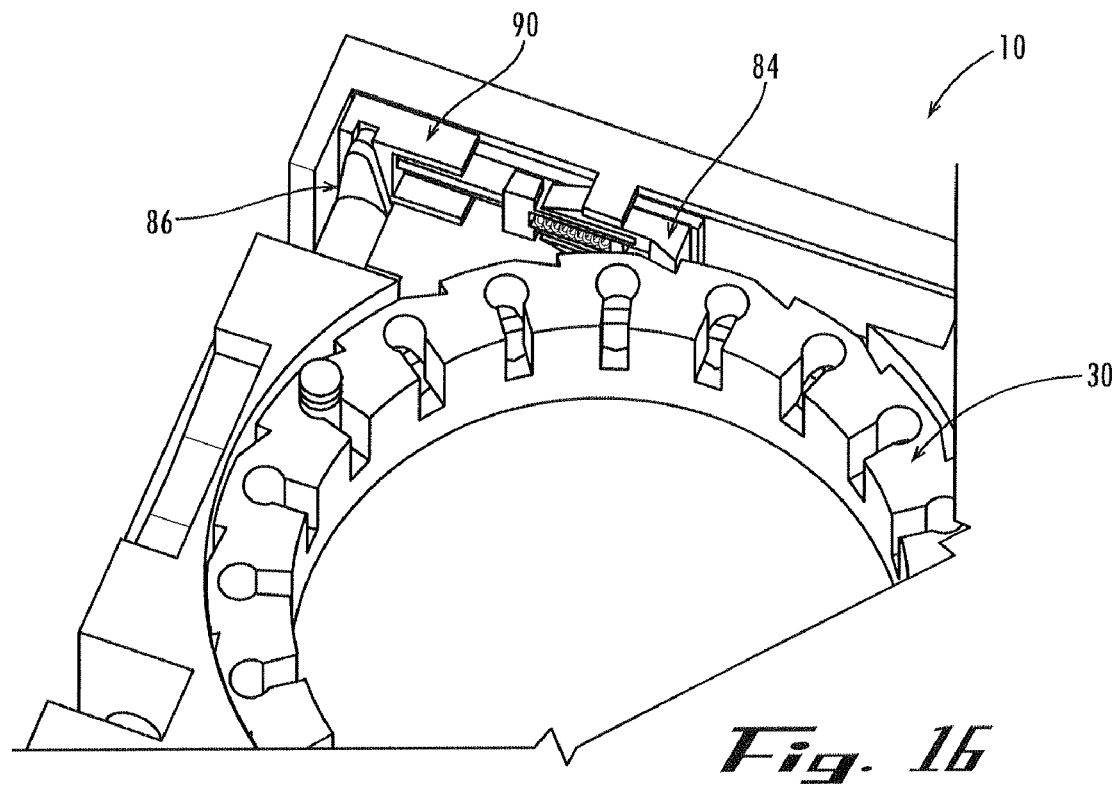
FIG. 16 is a perspective view of the portion of the lancing device of FIG. 12, showing the lancet register member returned to the position of FIG. 12 when the housing lid and cap-engaging member are rotated through the first motion.

FIG. 16 shows the lancet register member 84 returned to the start position of FIG. 12. When the housing lid and cap-engaging member are rotated through the first motion and back to the first/open position of FIG. 8, the advancing arm 86 is rotated to laterally pull the slide member 90 and the register member 84 back to the start position. The process is repeated after the next lancet is used and the advancing mechanism 18 is operated.

Figure 19:
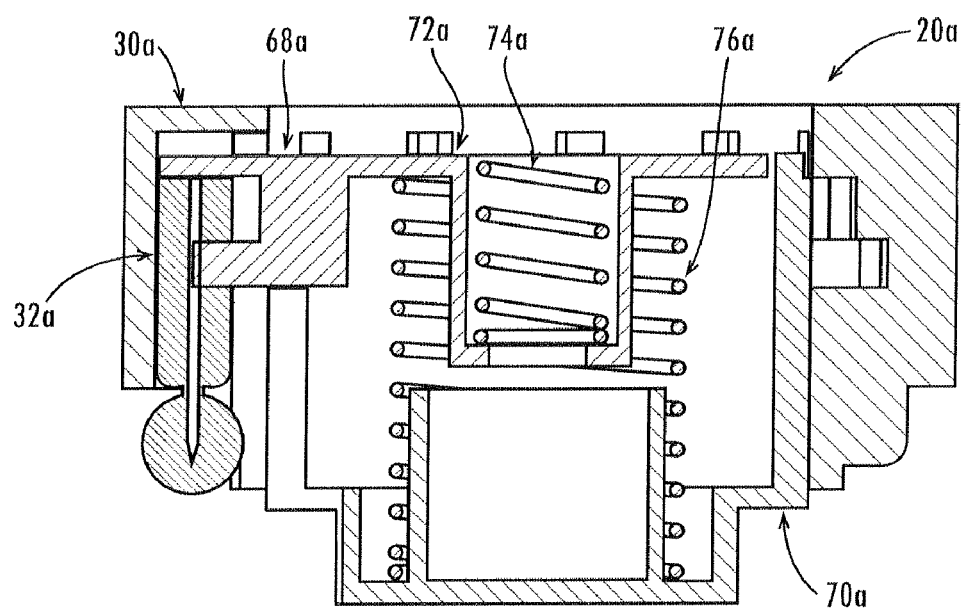
FIG. 19 is a side view of an alternative drive mechanism that can be used in the lancing device of FIG. 1.

Turning now to FIG. 19, there is shown an alternative drive mechanism 20a that can be used interchangeably in the lancing device 10. The drive mechanism 20a is operable with the same carrier 30a holding lancets 32a. In this embodiment, however, the drive spring 74a and the return spring 76a are coaxially arranged. And the drive member 68a and the spring arm 72a are provided as a unitary piece that move together in the lancet stroke direction.

Figure 20:
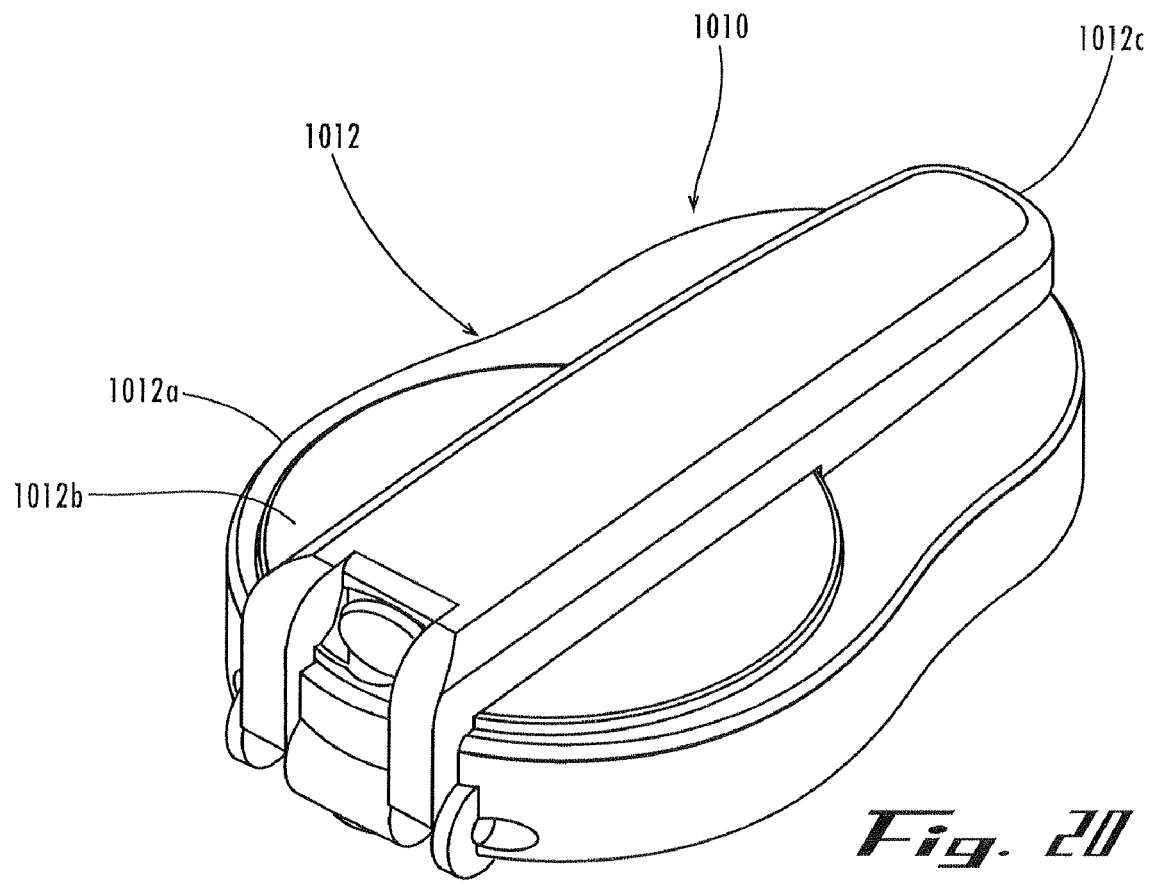
FIG. 20 is a perspective view of a lancing device according to a second example embodiment of the present invention, showing the device assembled for use.
Figure 21:
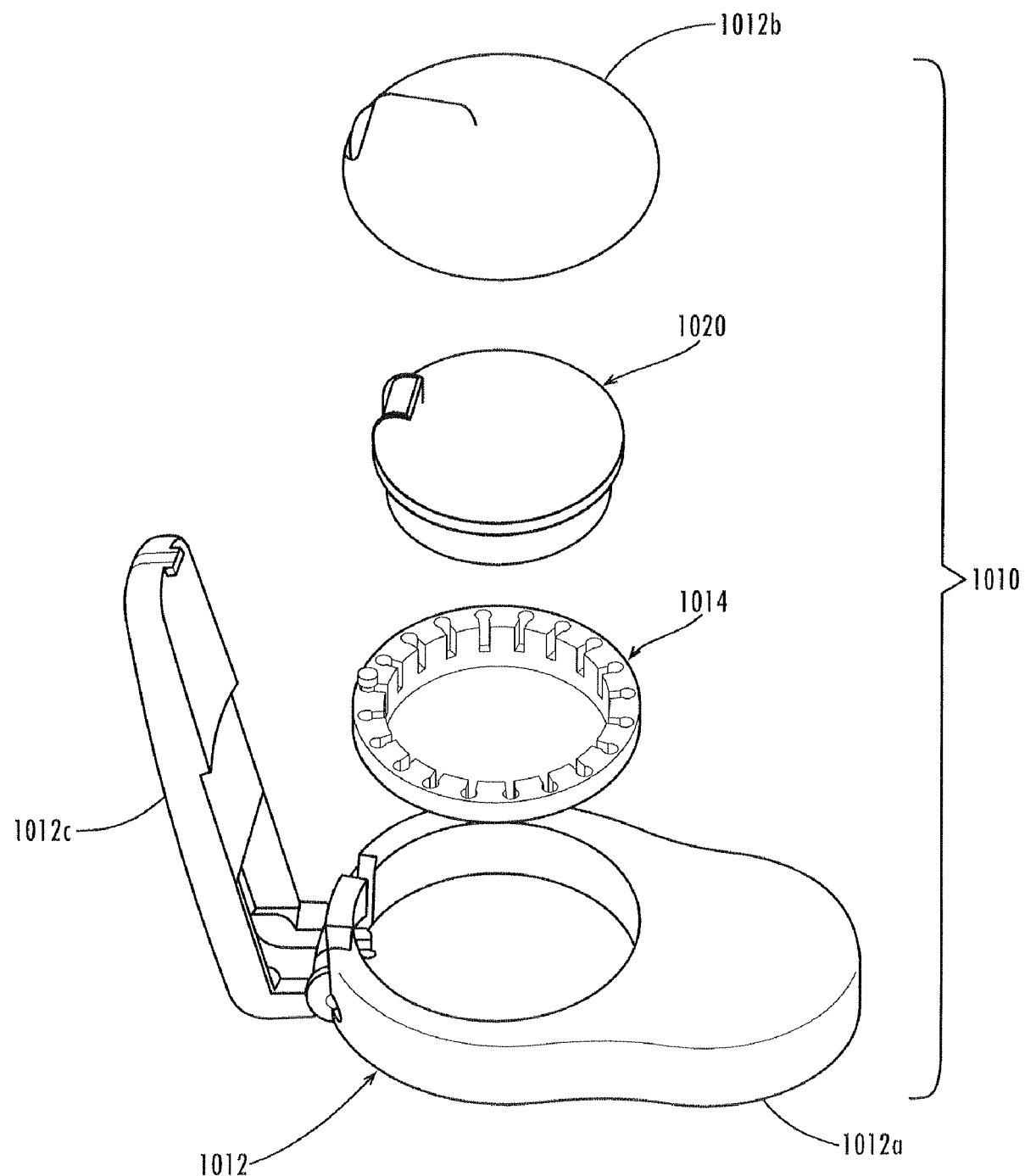
FIG. 21 is a perspective exploded view of the lancing device of FIG. 20, showing the major components of the device.
Figure 22:
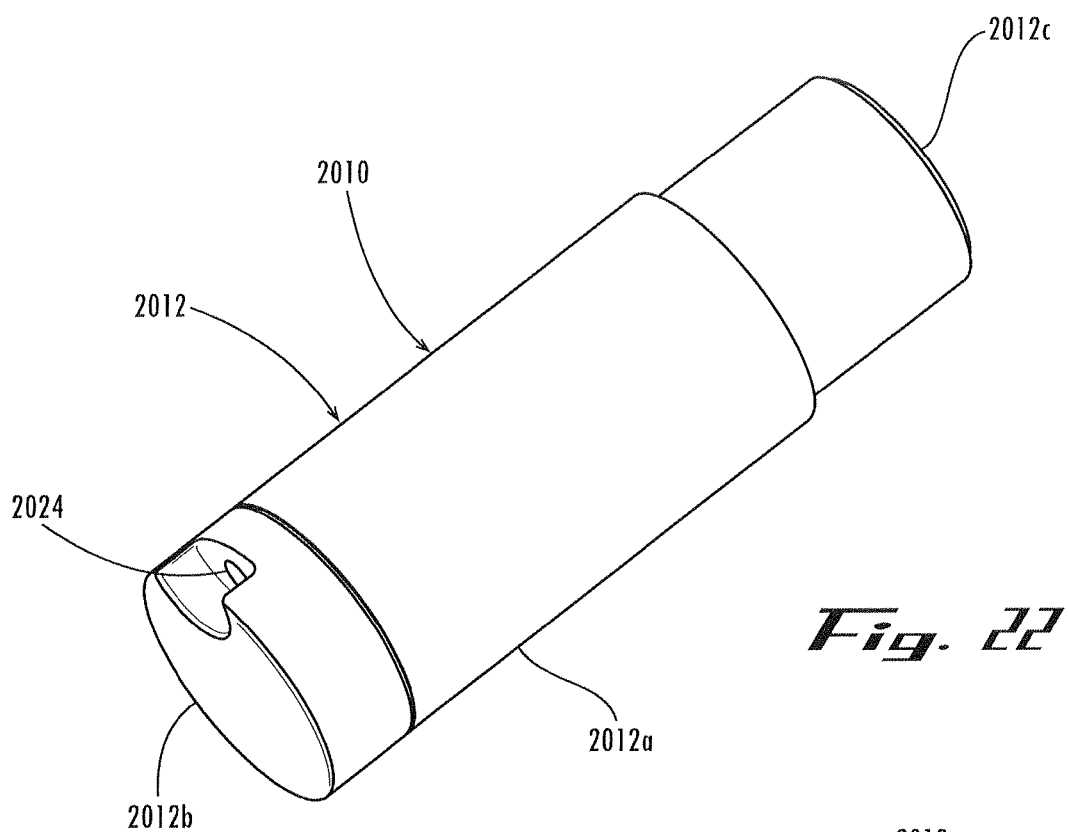
FIG. 22 is a perspective view of a lancing device according to a third example embodiment of the present invention, showing the device assembled for use.
Figure 23:
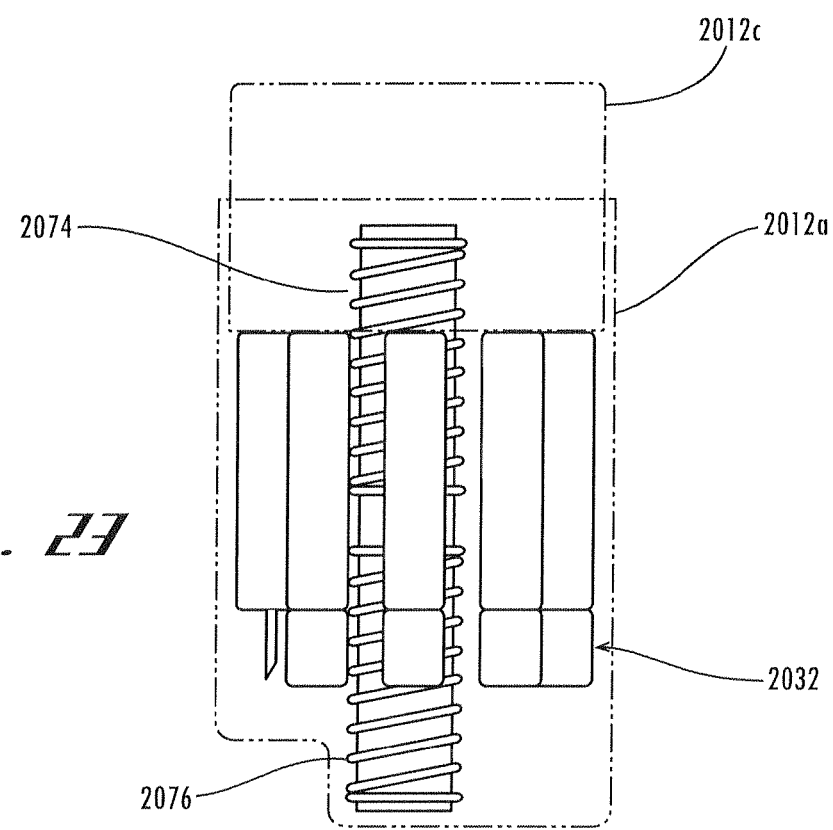
FIG. 23 is a side view of the lancing device of FIG. 22, showing the major internal components of the device.

Referring now to FIGS. 20 and 21, there is shown a lancing device 1010 according to a second example embodiment of the invention. Similarly to the lancing device 10 of the first embodiment, this lancing device 1010 has a housing 1012 with a base 1012a and a lid 1012b, a lancet carousel 1014, and a drive mechanism 1020. In this embodiment, however, the lancing device 1010 has an actuating member 1012c that is separate and distinct from the housing lid 1012b. In this way, the lancet carousel 1014 is not exposed (by opening the lid 1012b) every time the user advances a fresh lancet for use.

Referring now to FIGS. 22-25, there is shown a lancing device 2010 according to a third example embodiment of the invention. Somewhat similarly to the lancing device 1010 of the second embodiment, this lancing device 2010 has a housing 1212 with a base 2012a, a removable lid 1012b, and an actuating member 2012c. The housing 2012 has an opening 2024 for sequentially receiving the lancets 2032 loaded onto the carrier 2030 of a lancet carousel 2014. The drive mechanism includes a drive spring 2074 and a return spring 2076 that are charged to move a drive member 2068. The drive member 2068 has a plurality of parallel lancet openings 2069 and the lancet openings 2046 of the carrier 2030 are alignable with the drive member lancet openings. In this way, the carrier 2030 can be inserted into the housing 2012 with the lancets 2032 received through the aligned sets of openings 2046 and 2069.

In addition, the lancing device 2010 includes a lancet advancing mechanism having a cam path 2085 that cooperatively engages one or more followers 2087. The cam path 2030 may be defined by an interior wall of the housing 2012 and the followers 2087 may extend from the drive member 2068, or vice versa. The lancet advancing mechanism further includes a ramped cam member 2093 that is cooperatively engaged by one or more register members 2091. The ramped cam member 2093 may extend from the drive member 2068 and the register members 2091 may extend from the actuating member 2012c, or vice versa. When the user depresses the actuating member 2012c, the register members 2091 contact and slide along the ramped cam member 2093, which causes the drive member 2068 and lancet carousel 2014 to turn in the direction of arrow 2095. The cam surface 2085 then leads the follower 2087 and the drive member 2068 to move from the rest position 2085a to the charged position 2085b, which charges the drive spring 2074. Once the follower 2087 is turned just past the charged position 2085b, it is free to move within the cam surface 2085 in the direction of the lancing stroke. The drive member 2068 and lancet carousel 2014 are thereby released to be launched by the charged drive spring 2074 to the fully extended lancing position 2087c. The return spring 2076 then retracts the drive member 2068 and lancet carousel 2014 back to the rest position 12a, and then the process is repeated until the lancet carousel is spent. With the cam surface 2085 in this configuration, the lancets 2032 are sequentially charged, launched, and advanced all by once depressing the actuator member 2012c.

Referring now to FIGS. 26-57, there is shown a lancing device 3010 according to a fourth example embodiment of the invention. Similarly to the lancing device 10 of the first embodiment, this lancing device 3010 has a housing 3012 with a base 3012a and a lid 3012b, a lancet carousel 3014, a sterility cap repositioning mechanism 3016, a lancet advancing mechanism 3018, and a drive mechanism 3020. In this embodiment, however, there are modifications in the sterility cap repositioning mechanism 3016, the lancet advancing mechanism 3018, and the drive mechanism 3020.

Figure 26:
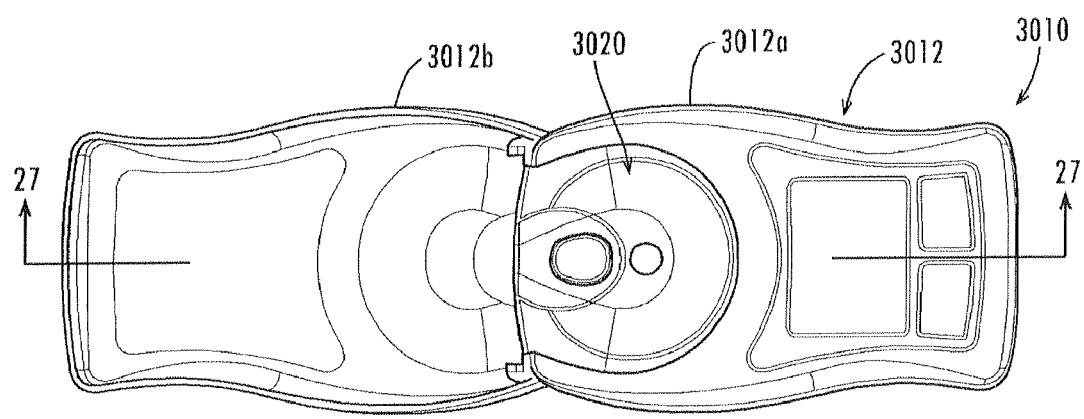
FIG. 26 is a plan view of a lancing device according to a fourth example embodiment of the present invention, showing a housing lid in a first/open position and a cap-engaging member of a sterility cap repositioning mechanism in a first position.
Figure 27:
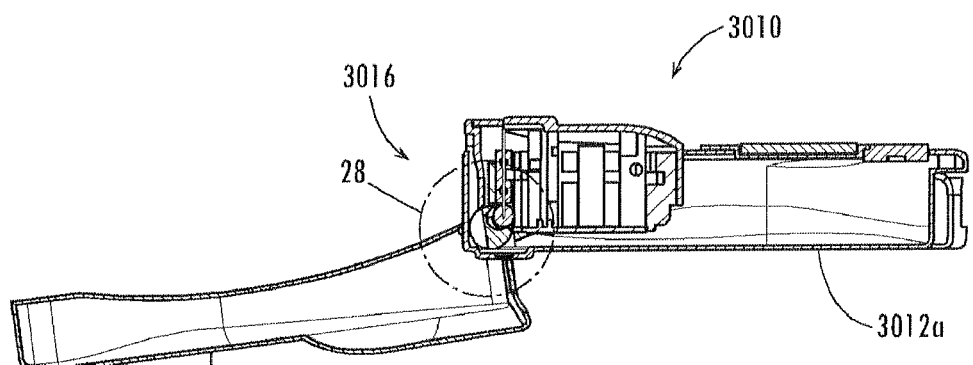
FIG. 27 is a cross-sectional side view of the lancing device taken at line 27-27 of FIG. 26.
Figure 28:
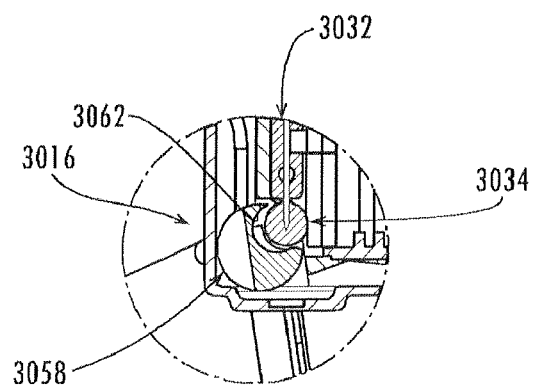
FIG. 28 is a detail view of a portion of the lancing device of FIG. 27, showing the cap-engaging member engaging the cap.
Figure 29:
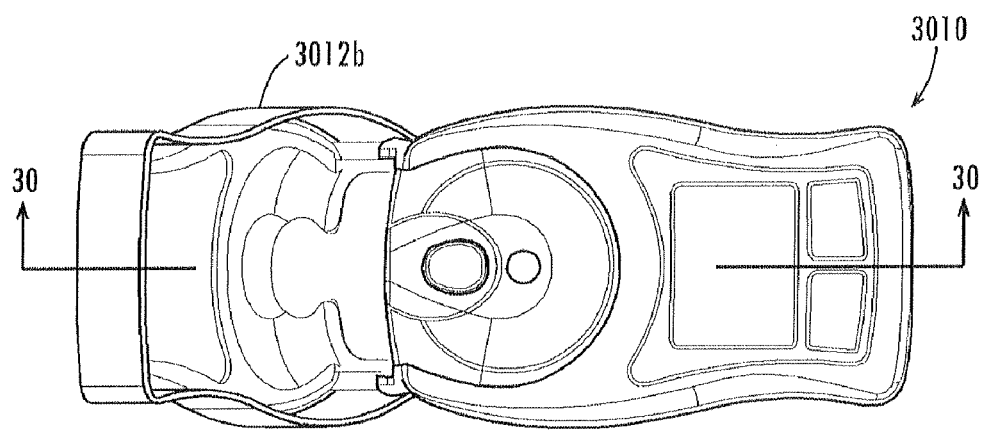
FIG. 29 is a plan view of the lancing device of FIG. 29, showing the cap-engaging member and the housing lid being rotated through the first motion to remove the lancet cap.
Figure 30:
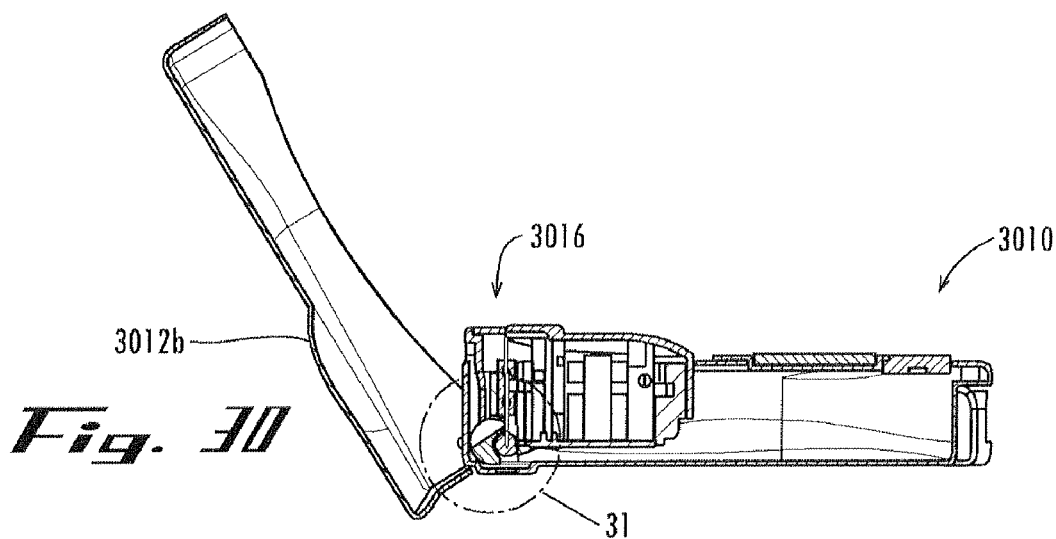
FIG. 30 is a cross-sectional side view of the lancing device taken at line 30-30 of FIG. 29.
Figure 31:
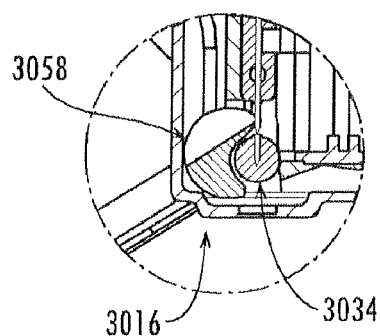
FIG. 31 is a detail view of a portion of the lancing device of FIG. 29, showing the cap-engaging member removing the cap from the lancet.
Figure 32:
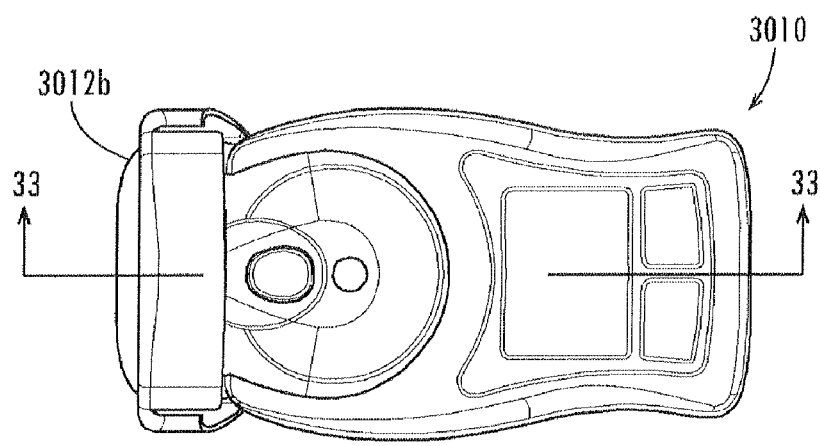
FIG. 32 is a plan view of the lancing device of FIG. 29, showing the cap-engaging member and the housing lid being rotated further in the first motion to remove the lancet cap.
Figure 33:
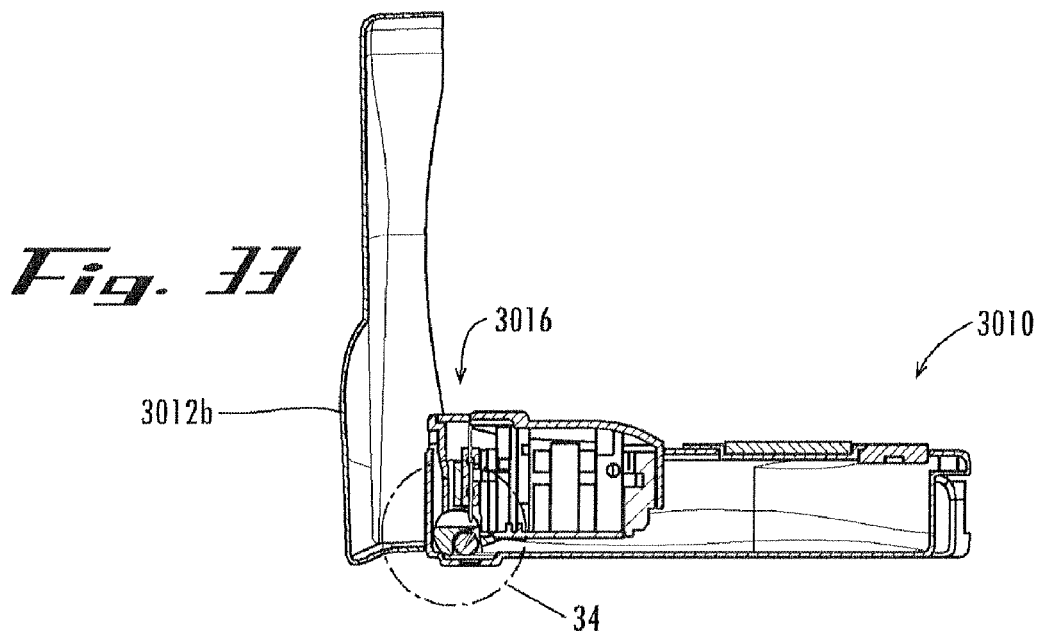
FIG. 33 is a cross-sectional side view of the lancing device taken at line 33-33 of FIG. 29.
Figure 34:
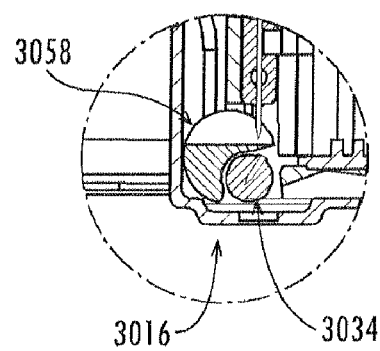
FIG. 34 is a detail view of a portion of the lancing device of FIG. 29, showing the cap removed off of the lancet by the cap-engaging member.
Figure 35:
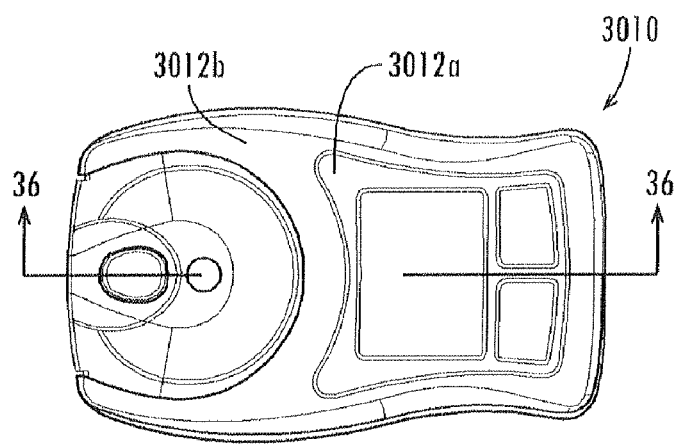
FIG. 35 is a plan view of the lancing device of FIG. 29, showing the cap-engaging member in the de-capped position with the lancet cap removed from the lancet tip, the housing lid in the closed position, and the lancet still in the set position.
Figure 36:
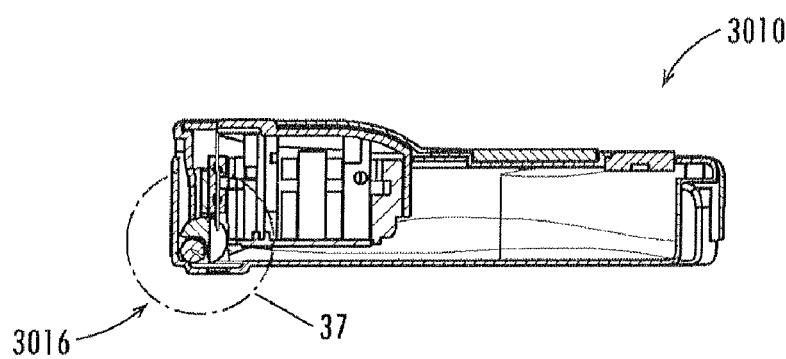
FIG. 36 is a cross-sectional side view of the lancing device taken at line 36-36 of FIG. 29.

FIGS. 26-39 show the structure and operation of the sterility cap repositioning mechanism 3016. FIGS. 26-28 show the sterility cap repositioning mechanism 3016 in a position corresponding to FIG. 6, with the cap-engaging member 3058 in the capped position with its cap opening 3062 receiving the lancet cap 3034, the housing lid 3012b in the open position, and the lancet 3032 in the set position. FIGS. 29-31 show the sterility cap repositioning mechanism 3016 with the cap-engaging member 3058 and the housing lid 3012b being rotated through the first motion to remove the lancet cap 3034. FIGS. 32-34 show the sterility cap repositioning mechanism 3016 in a position corresponding to FIG. 7, with the cap-engaging member 3058 and the housing lid 3012b being rotated further in the first motion to remove the lancet cap 3034. And FIGS. 35-38 show the sterility cap repositioning mechanism 3016 in a position corresponding to FIG. 8, with the cap-engaging member 3058 in the de-capped position with the lancet cap 3034 removed from the lancet tip 3036, the housing lid 3012b in the closed position, and the lancet 3032 still in the set position.

Figure 37:
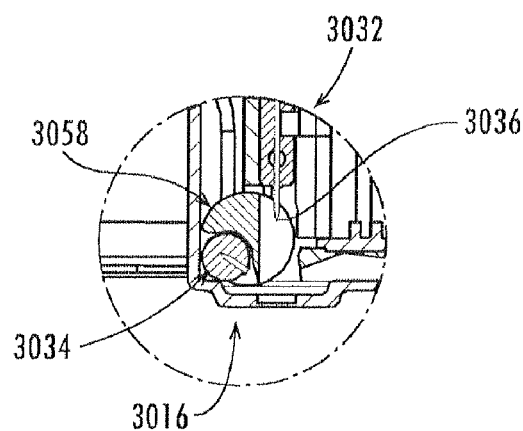
FIG. 37 is a detail view of a portion of the lancing device of FIG. 29, showing the cap removed and retained in the housing.
Figure 38:
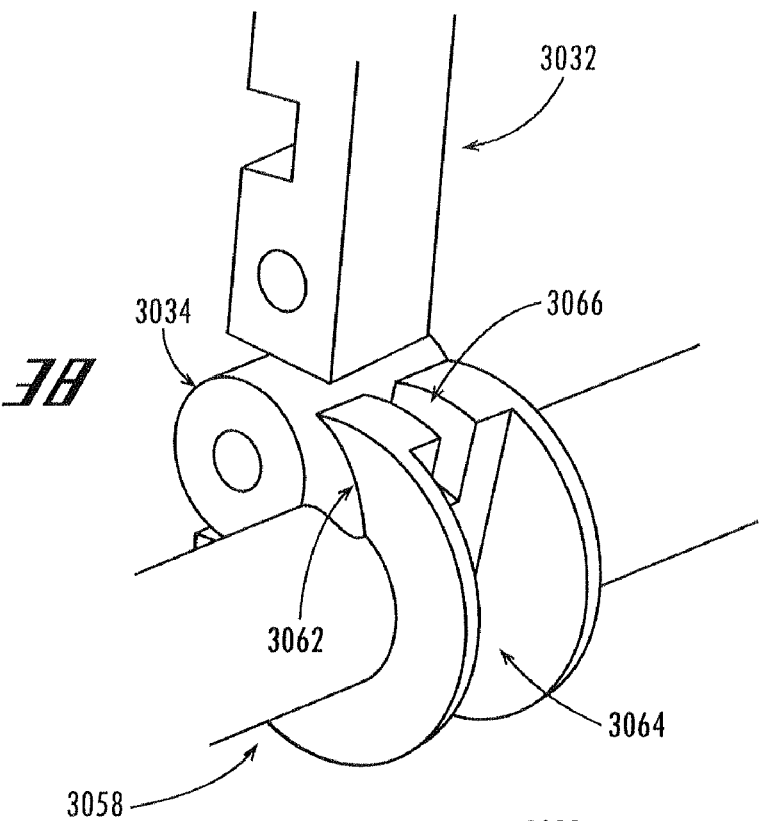
FIG. 38 is a perspective view of a portion of the cap-engaging member of FIG. 29 in the first position.
Figure 39:
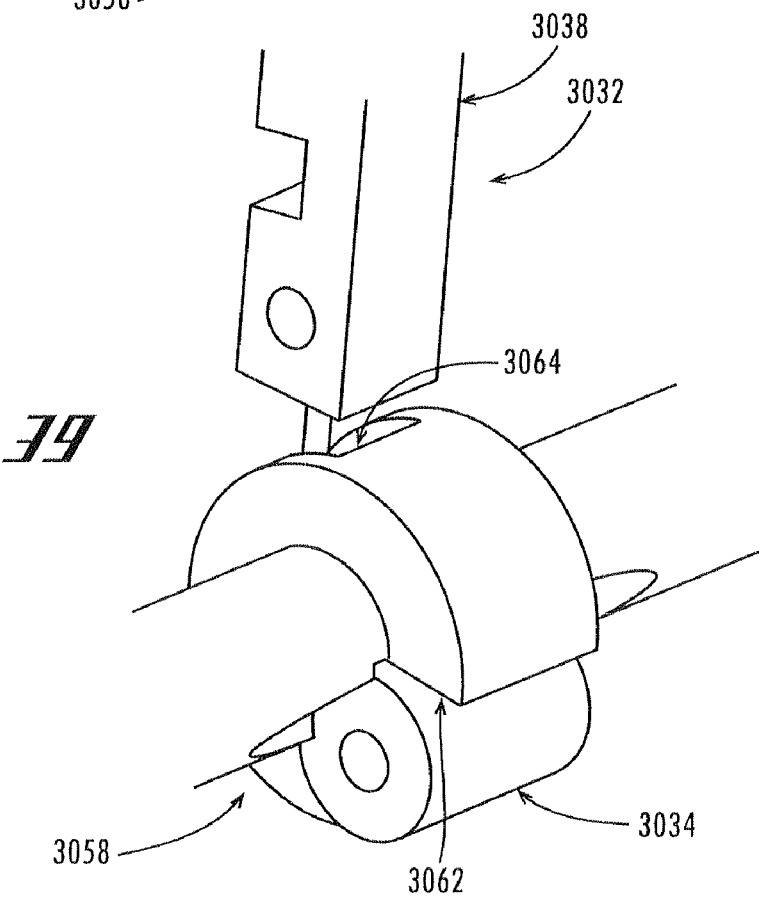
FIG. 39 is a perspective view of a portion of the cap-engaging member of FIG. 29 in the second position.

In addition, FIGS. 38 and 39 correspond to FIGS. 28 and 37, respectively, and show details of the cap-engaging member 3058 including its cap opening 3062, its body opening 3064, and its channel 3066. As can be seen in the figures, the lancet body 3038 has a generally rectangular profile and so too does the body opening 3064. And the cap 3034 is generally cylindrical but has a generally circular profile, so the cap opening 3064 has a semi-circular profile too.

Figure 41:
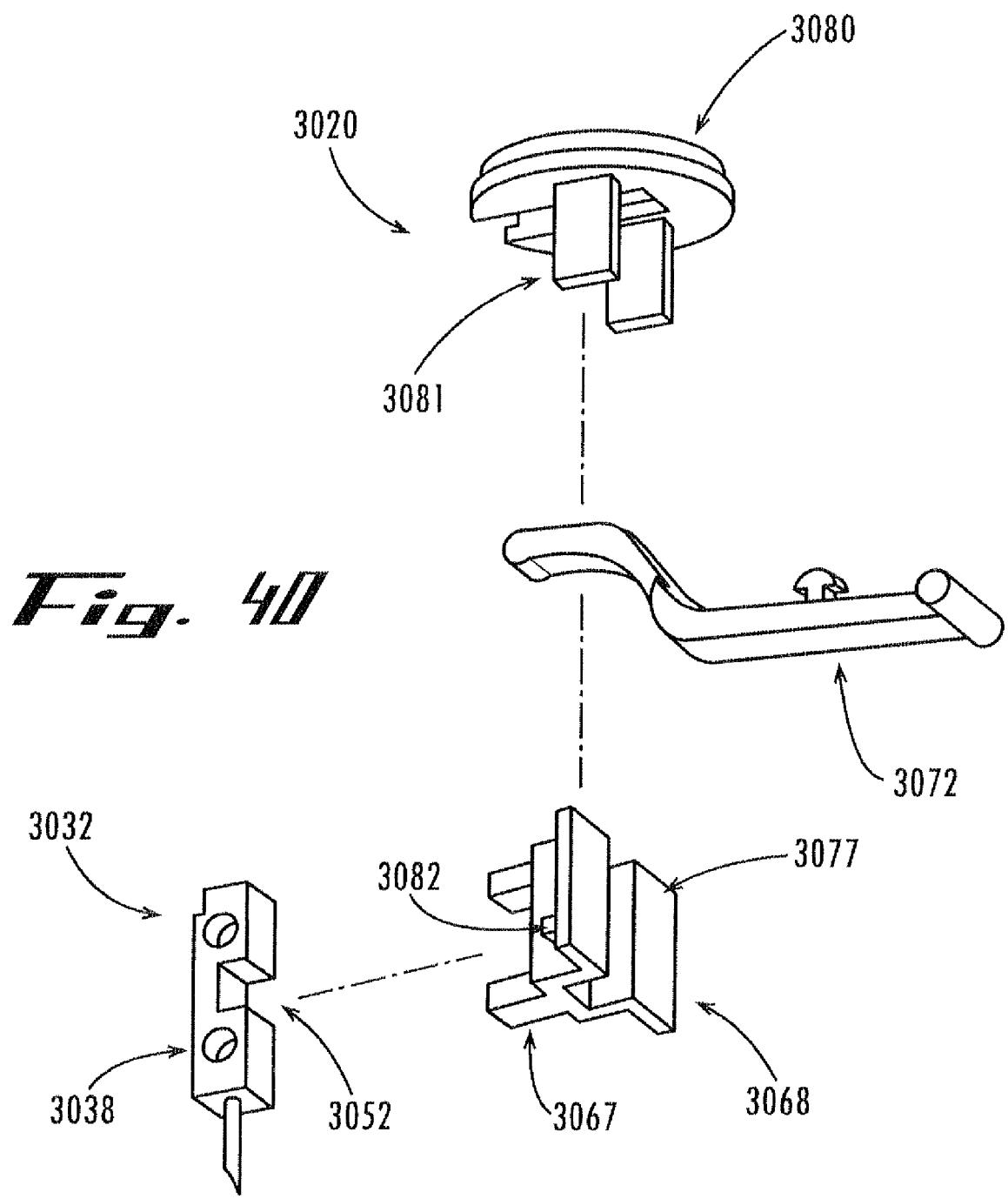
FIG. 41 is a cross-sectional view of the drive mechanism of FIG. 40, showing the drive spring uncharged.
Figure 41:
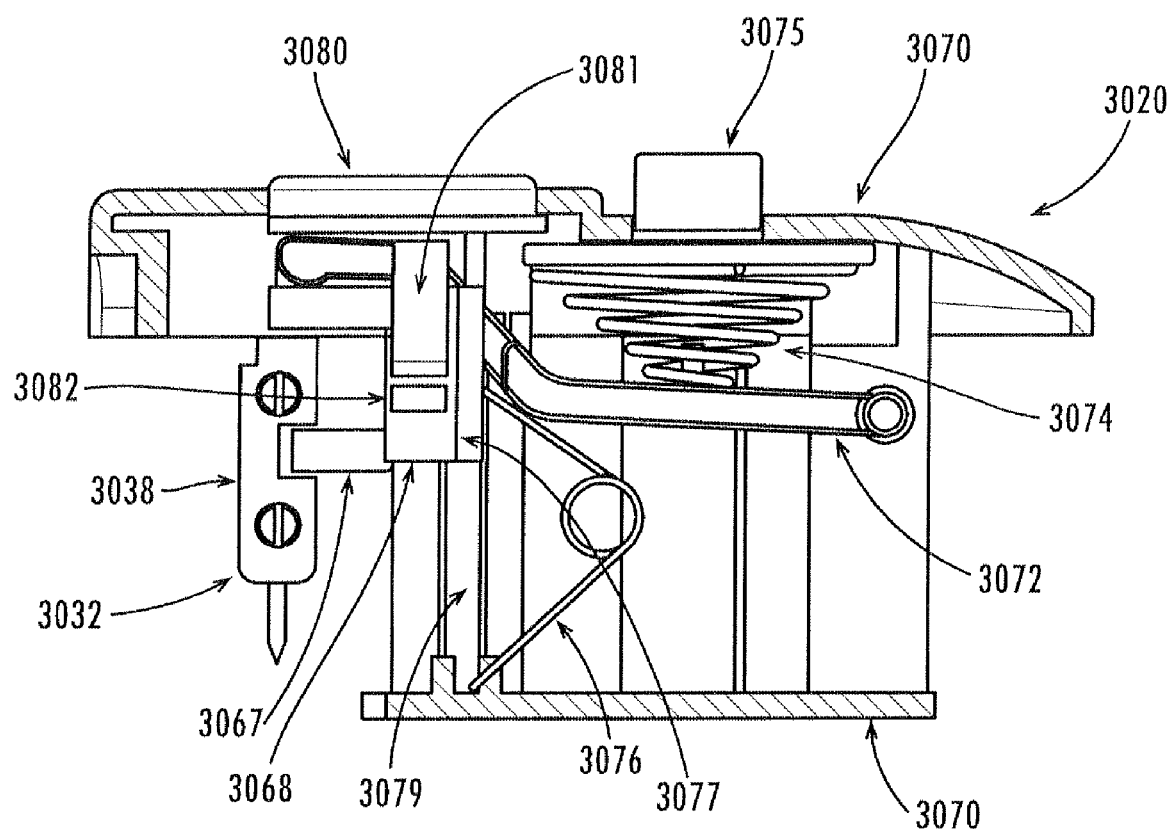

FIGS. 40-49 show the operation of the drive mechanism 3020. FIGS. 40 and 41 show the major components of the drive mechanism 3020, which include the drive member 3068, the frame 3070, the spring arm 3072, the drive spring 3074, the return spring 3076, the releasable catch members 3078 (see FIGS. 43-45), and the drive actuating member 3080. The spring arm 3072 is biased by the drive spring 3074 and the return spring 3076. The drive spring 3074 is preferably a compression spring and the return spring 3076 is preferably a torsion spring, as shown. A plunger 3075 engages the drive spring and extends from the frame 3070 for operable engagement by the housing lid. The releasable catch members 3078 releasably engage the drive member 3068 in the set position by, for example, the catches 3082 shown on the drive member. The drive actuating member 3080 has actuating arms 3081 that contact and spread the releasable catch members 3078 to release them from the catches 3082 on the drive member 3068. The drive member 3068 has guide arms 3077 that ride in guide slots 3079 in the frame 3070. And the drive arm 3052 of the lancet 3032 engages the drive notch 3067 of the drive member 3068.

Figure 42:
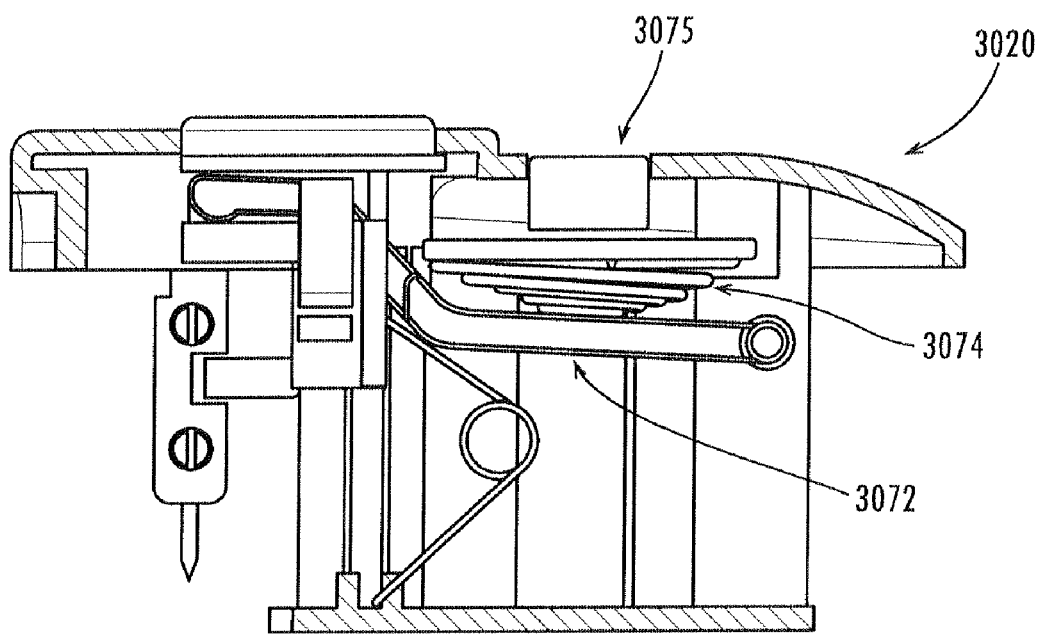
FIG. 42 is a cross-sectional view of the drive mechanism of FIG. 40, showing the drive spring charged by the plunger being engaged and depressed by the housing lid.
Figure 43:
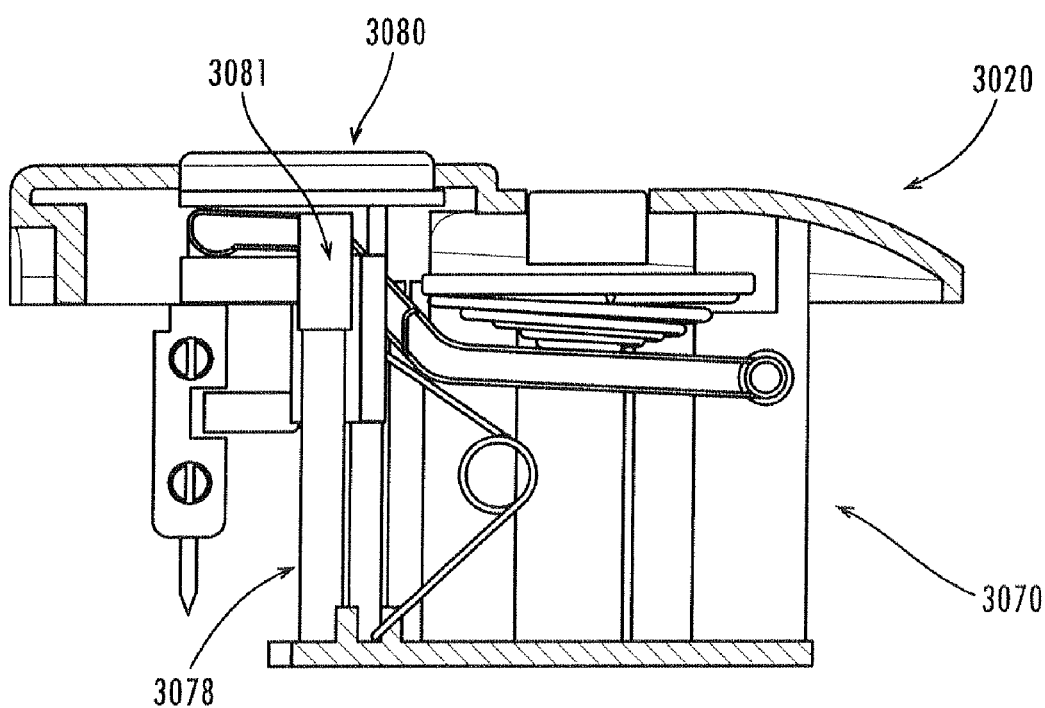
FIG. 43 is a cross-sectional view of the drive mechanism of FIG. 40, showing the same structure as in FIG. 42 but additionally showing the release members.
Figure 44:
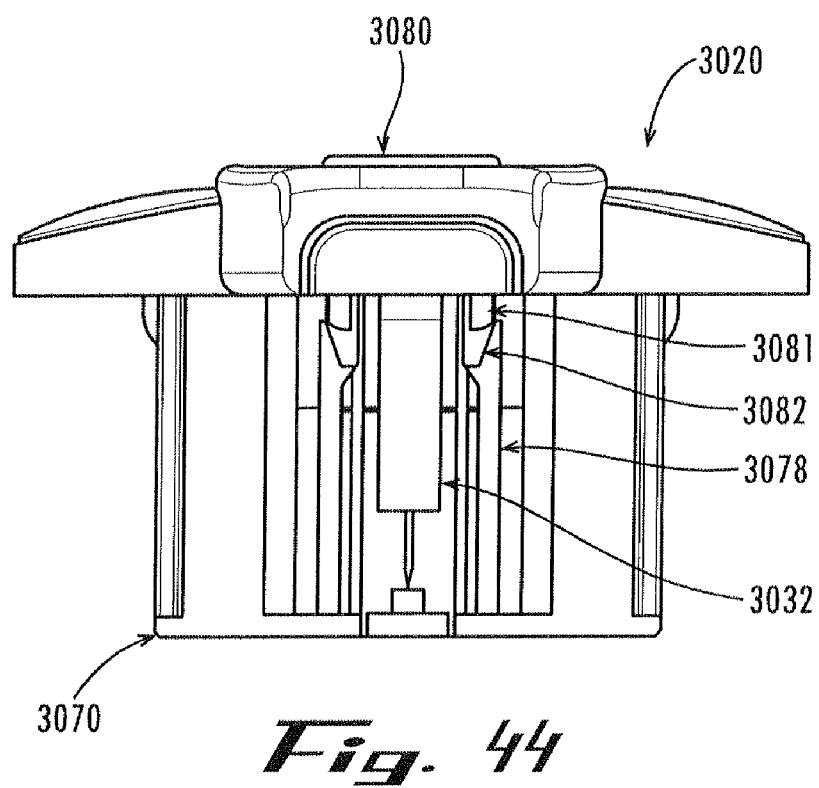
FIG. 44 is a front view of the drive mechanism of FIG. 43, showing the release members retaining the lancet in place.
Figure 45:
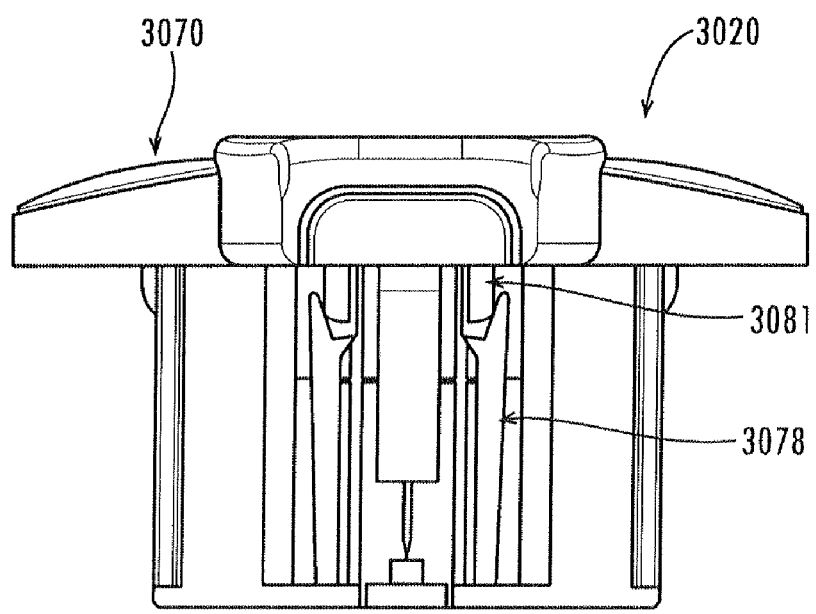
FIG. 45 is a front view of the drive mechanism of FIG. 44, showing the release members being released so the lancet can be launched.
Figure 46:
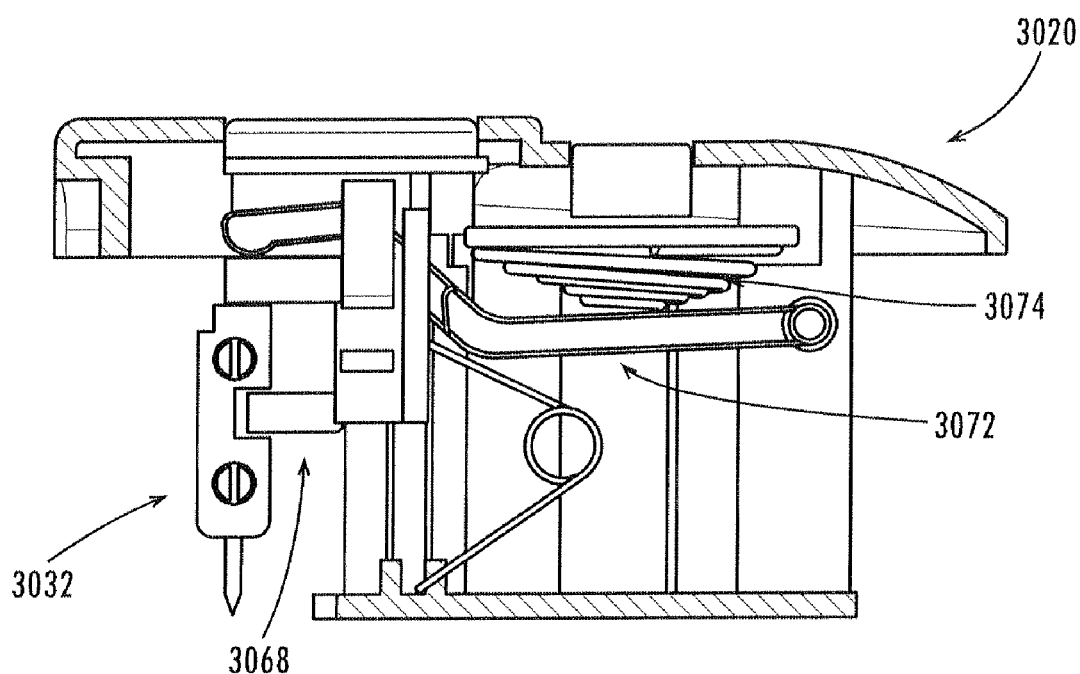
FIG. 46 is a cross-sectional view of the drive mechanism of FIG. 40, showing the lancet being launched.
Figure 47:
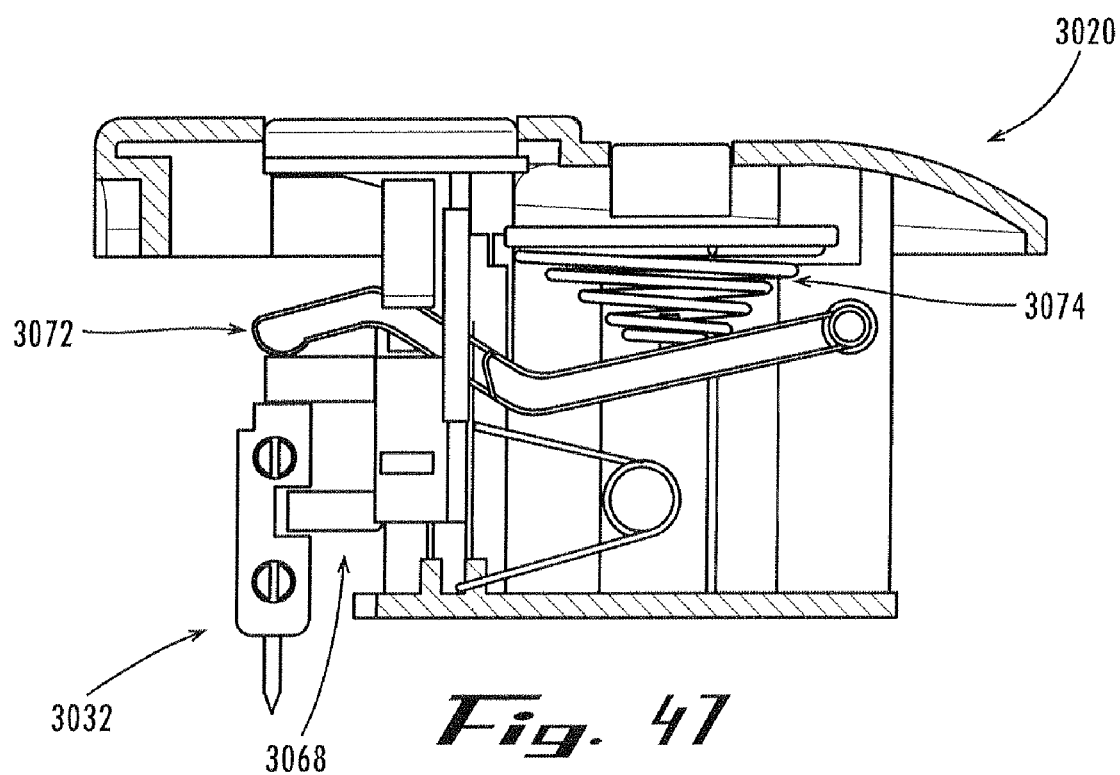
FIG. 47 is a cross-sectional view of the drive mechanism of FIG. 40, showing the lancet traveling through its puncture stroke.
Figure 48:
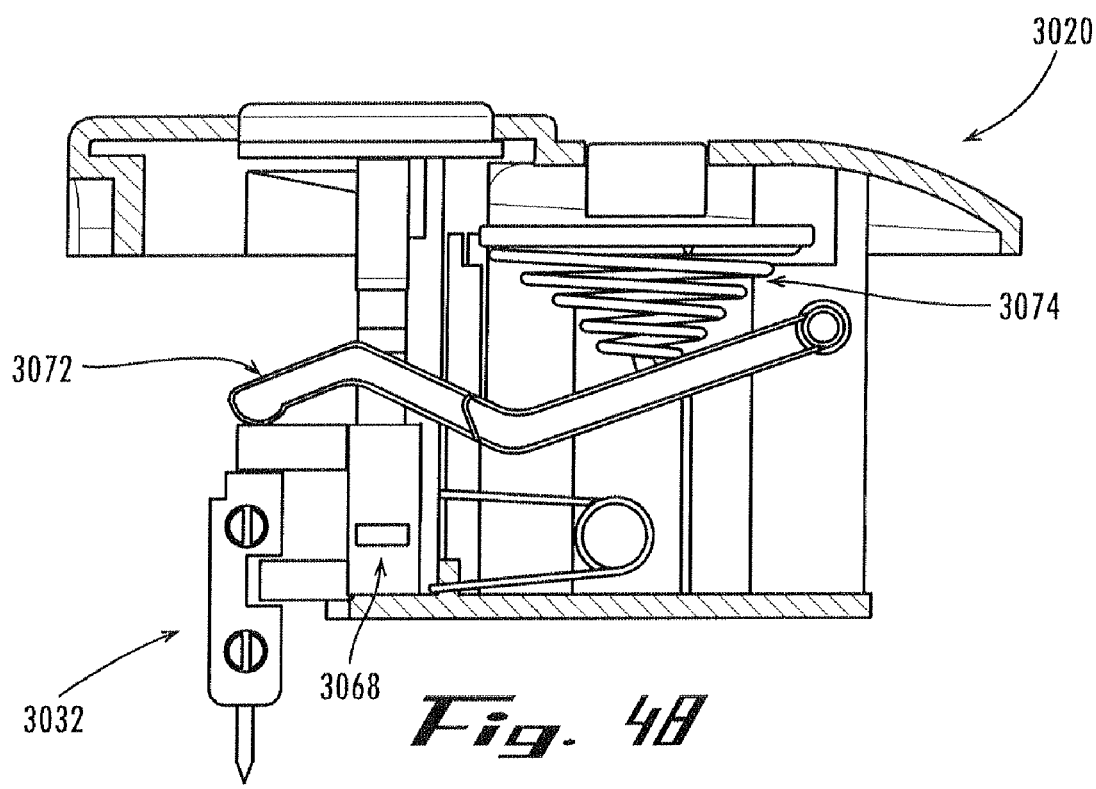
FIG. 48 is a cross-sectional view of the drive mechanism of FIG. 40, showing the lancet in the puncturing position.
Figure 49:
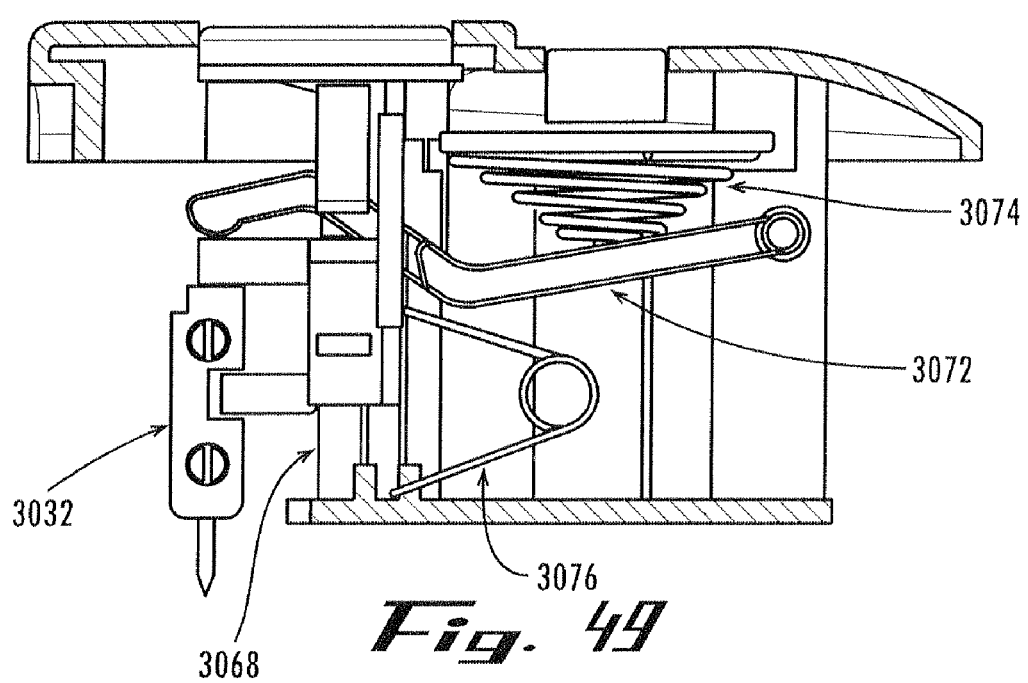
FIG. 49 is a cross-sectional view of the drive mechanism of FIG. 40, showing the lancet being retracted from the puncturing position.

As shown in FIG. 42, when the user moves the housing lid 3012b to the second/closed position, it engages the plunger 3075 to compress and charge the drive spring 3074 against the spring arm 3072, thereby charging the drive member 3068. FIGS. 43 and 44 show the drive mechanism 3020 in the same position as in FIG. 42, but additionally show the release members 3078. FIG. 45 shows the drive mechanism 3020 being actuated to launch the lancet 3032. To do this, the user depresses the drive actuating member 3080, which pushes the actuating arms 3081 into contact with and spreads apart the release members 3078 from engagement with the catches 3082. Then the drive member 3068, charged by the drive spring 3074 via the spring arm 3072, launches the lancet 3032 through a puncturing stroke, as shown in FIGS. 46 and 47, to the puncturing position shown in FIG. 48. During the puncturing stroke, the lancet body 3038 passes through the body opening 3064 of the cap-engaging member 3058 (see FIG. 39).

Then the return spring 3076 retracts the lancet 3032 into the housing 3012 until the drive spring 3074 and the return spring reach a neutral, balanced position. In this embodiment, the lancets 3032 in this position cannot be advanced. This is because the drive notch 3052 of the lancet 3032 is not aligned with an interior circumferential drive channel (described below) in the carrier. Only after the housing lid 12b is opened, which relieves all charge on the drive spring 3074, does the return spring 3076 return the lancet 3032, the drive member 3068, and the spring arm 3072 to the set position. The drive mechanism 3020 is now ready for recharging when the housing lid 3012b is closed again to engage the plunger 3075 again.

FIGS. 50-56 show the structure and operation of the lancet advancing mechanism 3018. FIGS. 50 and 51 show the position of the lancet register member 3084 when the housing lid is in the second/closed position. Preferably, the lancet register member 3084 is operably coupled to the cap-engaging member so that the sterility cap repositioning mechanism 3016 and the lancet advancing mechanism 3018 are operated together by the same actuating member, which is the housing lid 3012b in this embodiment. For example, the lancet advancing mechanism 3018 may be coupled to the axle 3060 of the cap-engaging member 3058.

The lancet register member 3084 engages and advances the carrier 3030 to sequentially move the lancets into the set position for use. Thus, the lancet register member 3084 is configured to advance a first lancet out of engagement with the drive member and to advance a second lancet into engagement with the drive member during the second motion after the first lancet has been re-capped and reset. Preferably, the register member 3084 includes a ramp 3088 that releasably engages the preferred ramp-notched register surfaces 3056 of the carrier 3030 (see FIG. 54).

Figure 52:
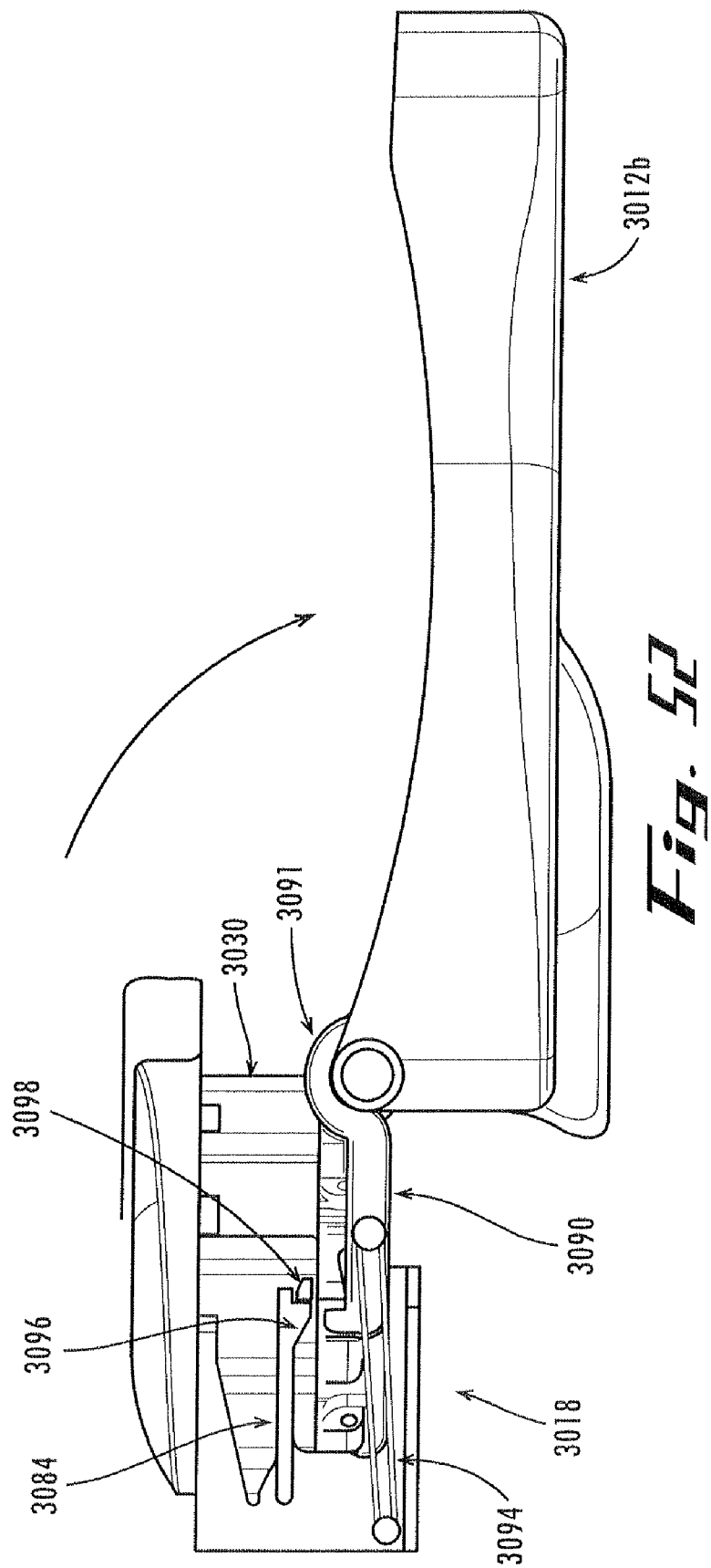
FIG. 52 is a side view of the lancet advancing mechanism of FIG. 50, showing the register member being charged as the housing lid is rotated through the second motion.

Referring additionally to FIG. 52, there is shown the register member 3084 being charged as the housing lid 3012b is rotated through the second motion. The lancet advancing mechanism 3018 further includes an advancing actuator member 3090 that is eccentrically coupled to axle 3060 by an advancing arm 3086 so that rotation of the advancing arm pulls on the actuator member. The register member 3084 has an engagement surface 3096 that catches on a catch member 3098 on the housing, thereby retaining the register member in position. As the actuator member 3090 is moved away from the register member 3084, an advancing spring 3094 is tensioned and charged. The advancing spring 3094 may be a band of elastic material, a helical spring, or another spring element.

FIGS. 53 and 54 show the register member 3084 being released as the housing lid is rotated to the first/open position at the end of the second motion. The actuator member 3090 includes a looped section 3091 with an inner radius that generally matches the outer radius of the axel 3060, and with a center that is aligned with the axis of the remainder of the advancing arm and inset from the end of the actuator arm by the length of the advancing arm 3086. In this way, just before the lid 3012b reaches the first/open position shown, the looped section 3091 seats onto the axle 3060, so that further rotation of the axle and advancing arm causes the actuator member 3090 to rotate with the axle. When the actuator member 3090 rotates like this, an advancing release member 3100 on the actuator member is moved into engagement with, and deflects, the register member 3084, which releases the ramped engagement member 3096 to shoot past the catch member 3098 by the charged spring 3094 to the position shown in FIGS. 55 and 56. This movement by the register member 3084 rotates the carrier 3030 (in the direction of arrow 3102) by one lancet position, so that the next lancet is now in the set position, engaged by the drive member and ready for use.

When the housing lid 3012b is rotated through the first motion and back to the first/open position of FIGS. 50 and 51, the advancing arm 3086 is rotated to push the actuator member 3090 and the register member 3084 back to the start position. The process is repeated after the next lancet is used and the advancing mechanism 3018 is operated.

Figure 57:
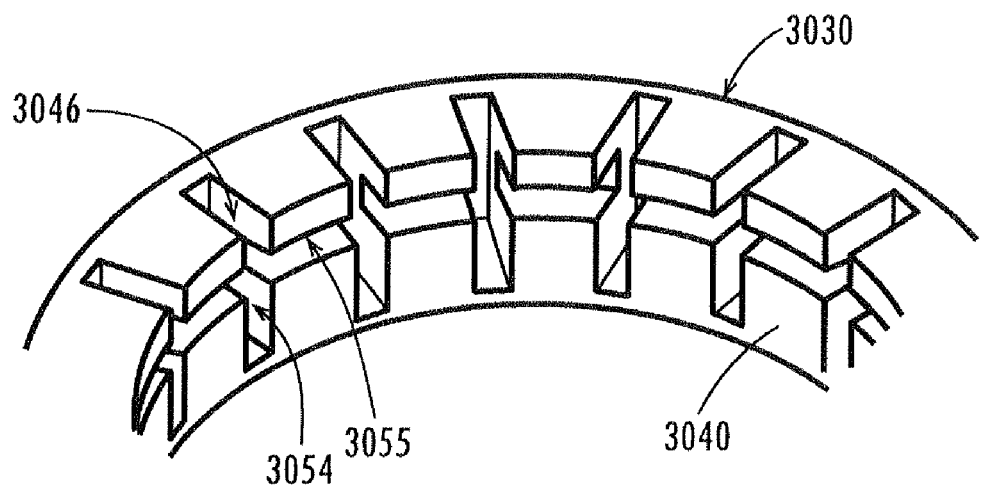
FIG. 57 is a detail perspective view of a portion of the carrier of the lancing device of FIG. 29, showing an interior circumferential drive channel in the carrier.
Figure 58:
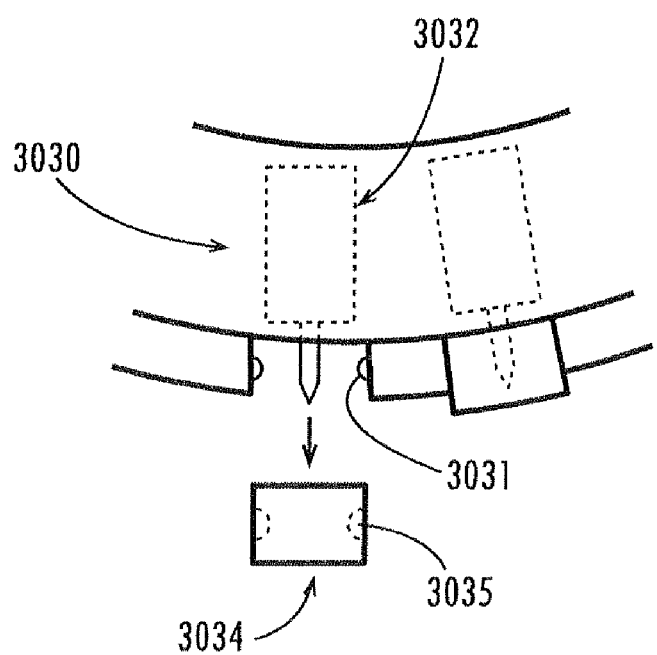
FIG. 58 is a detail side view of a portion of the carrier of the lancing device of FIG. 29, showing detents for holding the lancets in the carrier.

FIGS. 57 and 58 show additional details of the carrier 3030. In FIG. 57, there is shown the interior circumferential drive channel in the inner surface 3040 of the carrier 3030. As described above with reference to the drive mechanism 3020, when one of the lancets 3032 is retracted back into the housing 3012 and it lancet opening 3046 after firing, it returns to a neutral, balanced position. Then after the housing lid 3012b is opened, which relieves all charge on the drive spring, the return spring returns the lancet 3032, the drive member, and the spring arm to the set position, with the drive member moving up through the lateral opening 3054. In the set position, the drive notch of the lancet is now aligned with the interior circumferential drive channel 3055 in the carrier 3030. So the carrier 3030 can now be rotationally advanced, because the drive member can now pass laterally out of the drive notch of the just-used lancet, through the interior circumferential drive channel 3055, and into the drive notch of a next lancet.

In FIG. 58, there are shown retainers or detents that releasably hold the sterility caps 3034 to the carrier 3030. For example, the retainers or detents can be provided by male protrusions 3031 from inner walls of recesses on the carrier 3030 that engage female wells 3035 in the caps 3034, or vice versa. The retainers or detents provide enough holding force so that the lancets 3032 are held in the carrier 3030 with an interference or press fit. When the caps 3034 are removed from the lancet 3032, the lancets are free to move within the lancet openings for puncturing. Then after re-capping the lancets 3032, the caps 3034 now hold the lancets in place again.

Accordingly, it can be seen that the present invention provides a number of advantages over the known lancing devices. In the various aspects of the various example embodiments described herein, there is provided a lancet carousel that advantageously permits de-capping, charging, actuating, and re-capping of a lancet in the carousel, and then advancing a next lancet in the carousel for use. In addition, there is provided a lancing device with an innovative sterility cap repositioning mechanism and lancet advancing mechanism that increase the convenience of use to facilitate taking multiple blood samples without the risk of infection or contamination.

While the invention has been described with reference to preferred and example embodiments, it will be understood by those skilled in the art that a variety of modifications, additions and deletions are within the scope of the invention, as defined by the following claims.

What is claimed is:

1. A lancing device for use with at least one lancet having a lancet tip held by a lancet body and covered by a sterility cap, the lancing device comprising:
   a housing defining an opening through which the lancet tip can extend to lance skin, and configured for receiving the lancet with the sterility cap at least partially between the lancet tip and the housing opening; and
   a sterility cap repositioning mechanism including a cap-engaging member that is coupled to the housing and operable to move from a first position adjacent the sterility cap on the lancet tip, through a first motion to engage and remove the sterility cap from the lancet tip, and to a second position wherein the sterility cap is repositioned from between the lancet tip and the opening, wherein the cap-engaging member in the second position retains the sterility cap within the housing, and wherein the cap-engaging member is rotationally coupled to the housing and defines a cap opening configured to receive and engage the sterility cap, a body opening configured to receive the lancet body therethrough when the cap-engaging member is rotated to the second position and the lancing device is actuated, and a channel configured to receive the lancet tip therethrough when the cap-engaging member rotates through the first motion, wherein the channel extends between the cap opening and the body opening.

2. The lancing device of claim 1, wherein the cap-engaging member is further operable to move from the second position, through a second motion to replace the sterility cap on the lancet tip, and back to the first position.

3. The lancing device of claim 1, wherein the cap opening is curved.

4. The lancing device of claim 3, wherein the cap opening has a semi-circular profile.

5. The lancing device of claim 1, wherein the lancing device is operable to propel the lancet from a set position to lance skin, and wherein the cap-engaging member is operable to move the first lancet back to the set position during the second motion.

6. A lancing device for use with a plurality of lancets each having a lancet tip held by a lancet body and covered by a sterility cap, the lancing device comprising:
   a housing for carrying the plurality of lancets, the housing defining an opening through which a first lancet tip of a first one of the lancets can extend to lance skin in a lancing stroke, and configured for receiving the first lancet with the first sterility cap at least partially between the first lancet tip and the housing opening; and
   a sterility cap repositioning mechanism including a cap-engaging member that is coupled to the housing, and operable to move from a first position adjacent the first sterility cap on the first lancet tip, through a first motion to engage and remove the first sterility cap from the first lancet tip, and to a second position wherein the first sterility cap is repositioned from between the first lancet tip and the opening, wherein the cap-engaging member is rotationally coupled to the housing and defines a cap opening configured to receive and engage the first sterility cap, a body opening configured to receive the first lancet body therethrough during the lancing stroke when the cap-engaging member is rotated to the second position and the lancing device is actuated, and a channel configured to receive the first lancet tip therethrough when the cap-engaging member rotates through the first motion, wherein the channel extends between the cap opening and the body opening, and wherein the cap-engaging member in the second position retains the first sterility cap within the housing.

7. The lancing device of claim 6, wherein the cap-engaging member is further operable to move from the second position, through a second motion to replace the first sterility cap on the first lancet tip, and back to the first position.

8. The lancing device of claim 6, wherein the lancing device is operable to propel the first lancet from a set position to lance skin, and wherein the cap-engaging member is operable to move the first lancet back to the set position during the second motion.

9. The lancing device of claim 6, wherein the housing comprises a base and a lid, the base defining a chamber for the lancets, and the lid covering the chamber, wherein the lid is movably coupled to the base and fixedly coupled to the cap-engaging member so that the lid and the cap-engaging member move together, wherein moving the lid moves the cap-engaging member from the first position, through the first motion, and to the second position.

10. The lancing device of claim 6, wherein the cap-engaging member is further operable to move from the second position, through a second motion to replace the sterility cap on the lancet tip, and back to the first position.

11. The lancing device of claim 6, further comprising a carrier removably receivable in the housing, wherein the carrier is circular and has a rotational axis, and wherein the plurality of lancets are carried by the carrier in a parallel arrangement, wherein the lancets are coaxially arranged relative to the rotational axis.

12. The lancing device of claim 11, wherein the carrier is annular-shaped and defines a plurality of parallel lancet openings, wherein the lancets are received in the openings in a parallel arrangement and with a free-floating fit.

13. The lancing device of claim 12, wherein the carrier defines a circumferential recessed surface and the coaxial lancet openings extend through the recessed surface, wherein the lancet openings receive therein the lancet bodies and the recessed surface receives at least a portion of the sterility caps.

14. The lancing device of claim 13, wherein the circumferential recessed surface leaves exposed at least a portion of the sterility caps for engagement by the cap-engaging member.

15. The lancing device of claim 13, wherein each of the lancet openings forms a teardrop-shaped rim where it extends through the recessed surface of the carrier.

16. The lancing device of claim 12, further comprising a drive member, wherein the lancets each define a drive surface for engagement with the drive member to propel the lancets, and wherein the carrier defines an inner surface and a plurality of lateral openings extending between the inner surface and the lancet openings, wherein the lateral openings are configured to receive at least a portion of the drive member therethrough.

17. The lancing device of claim 11, further comprising a drive member and a register member, wherein the carrier defines a plurality of register surfaces with each one of the register surfaces indexed to a corresponding one of the lancet openings, and wherein the register surfaces are configured to sequentially engage the register member to advance the carrier from a first position with a first one of the lancets engaged by the drive member to a second position with a second one of the lancets engaged by the drive member.

18. The lancing device of claim 17, wherein the carrier defines an outer surface and the register surfaces comprise ramped notches defined in the outer surface.

19. The lancing device of claim 11, further comprising a drive member defining a plurality of parallel lancet openings, wherein the lancet openings in the carrier are alignable with the lancet openings in the drive member, wherein the carrier is insertable into the lancing device with the lancets received through the lancet openings in the carrier and the lancet openings in the drive member in a coaxial arrangement.

20. A lancing device for use with a plurality of lancets each having a lancet tip covered by a sterility cap, the lancing device comprising:

a housing for carrying the plurality of lancets, the housing defining an opening through which a first lancet tip of a first one of the lancets can extend to lance skin, and configured for receiving the first lancet with the first sterility cap at least partially the first lancet tip and the housing opening, wherein the housing comprises a base and a lid, the base defining a chamber for the lancets, and the lid covering the chamber; and a sterility cap repositioning mechanism including a cap-engaging member that is coupled to the housing, operable to move from a first position adjacent the first sterility cap on the first lancet tip, through a first motion to engage and remove the first sterility cap from the first lancet tip, and to a second position wherein the first sterility cap is repositioned from between the first lancet tip and the opening, wherein the cap-engaging member is further operable to move from the second position, through a second motion to replace the first sterility cap on the first lancet tip, and back to the first position, wherein the cap-engaging member defines a cap opening configured to receive and engage the first sterility cap, a body opening configured to receive the lancet body therethrough when the cap engaging-engaging member is rotated to the second position and the lancing device is actuated, and a channel configured to receive the lancet tip therethrough when the cap-engaging member rotates through the first motion, wherein the channel extends between the cap opening and the body opening, wherein the lid is movably coupled to the base and fixedly coupled to the cap-engaging member so that the lid and the cap-engaging member move together, wherein moving the lid moves the cap-engaging member from the first position, through the first motion, and to the second position.

21. A lancing device for use with at least one lancet having a lancet tip held by a body and covered by a sterility cap, the lancing device comprising:

a housing defining an opening through which the lancet tip can extend to lance skin in a lancing stroke, and configured for receiving the lancet with the sterility cap at least partially between the lancet tip and the housing opening; and a sterility cap repositioning mechanism including a cap-engaging member that is coupled to the housing and operable to move from a first position adjacent the sterility cap on the lancet tip, through a first motion to engage and remove the sterility cap from the lancet tip, and to a second position wherein the sterility cap is repositioned from between the lancet tip and the opening, wherein the cap-engaging member is further operable to move from the second position, through a second motion to replace the sterility cap on the lancet tip, and back to the first position, wherein the cap-engaging member defines a cap opening configured to receive and engage the sterility cap, wherein the cap-engaging member further comprises a channel configured to receive the lancet tip therethrough when the cap-engaging member moves through the first motion, wherein the channel extends between the cap opening and a body opening.

* * * * *